(12) United States Patent
Hergenrother et al.

(10) Patent No.: US 7,709,465 B2
(45) Date of Patent: May 4, 2010

(54) PHOSPHOROUS CONTAINING COMPOUNDS INCLUDING TRIPHENYLMETHYLPHOSPHONATE ESTERS FOR THE TREATMENT OF MELANOMA AND OTHER CANCERS

(75) Inventors: Paul J. Hergenrother, Champaign, IL (US); Vitaliy Nesterenko, Rantoul, IL (US); Karson S. Putt, Champaign, IL (US); Rahul Palchaudhuri, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 245 days.

(21) Appl. No.: 11/750,952

(22) Filed: May 18, 2007

(65) Prior Publication Data

US 2009/0004293 A1 Jan. 1, 2009

Related U.S. Application Data

(60) Provisional application No. 60/747,747, filed on May 19, 2006.

(51) Int. Cl.
*A61K 31/66* (2006.01)
*C07F 9/02* (2006.01)
(52) U.S. Cl. .................................. 514/129; 558/177
(58) Field of Classification Search .............. 558/177; 514/129
See application file for complete search history.

(56) References Cited

U.S. PATENT DOCUMENTS

| 3,360,432 | A | 12/1967 | Newallis et al. |
| 3,702,879 | A | 11/1972 | Hellmut et al. |
| 3,847,866 | A | 11/1974 | Iliopulos et al. |
| 3,879,498 | A | 4/1975 | Iliopulos et al. |
| 4,463,159 | A | 7/1984 | Besecke et al. |
| 5,569,673 | A | 10/1996 | Morre et al. |
| 6,090,796 | A | 7/2000 | Camden |
| 6,444,638 | B2 | 9/2002 | Schwartz et al. |
| 6,489,476 | B1 | 12/2002 | Dang et al. |
| 6,548,536 | B2 | 4/2003 | Hara et al. |
| 6,605,589 | B1 | 8/2003 | Uckun et al. |
| 6,608,026 | B1 | 8/2003 | Wang et al. |
| 6,627,623 | B2 | 9/2003 | Bai et al. |
| 2003/0148966 | A1 | 8/2003 | Jayaram et al. |
| 2003/0176506 | A1 | 9/2003 | Dawson et al. |
| 2003/0198949 | A1 | 10/2003 | Goldmakher et al. |
| 2005/0009816 | A1* | 1/2005 | Gouliaev et al. ......... 514/227.5 |
| 2005/0197511 | A1 | 9/2005 | Hergenrother et al. |

FOREIGN PATENT DOCUMENTS

| JP | 2002-123013 | 4/2002 |
| WO | WO 2005/044191 | 5/2005 |
| WO | WO 2005/086961 | 9/2005 |
| WO | WO 2005/090370 | 9/2005 |

OTHER PUBLICATIONS

Shi et al., 1990, CAS: 113: 24044.*
Nishimura et al., 1975, CAS: 83: 170942.*
Arbuzov et al., 1959, CAS: 53: 83200.*
U.S. Appl. No. 60/603,246, filed Aug. 20, 2004, Hergenrother et al.
U.S. Appl. No. 60/516,566, filed Oct. 30, 2003, Hergenrother et al.
Adjei et al. (2003) "Novel Anticancer Agents in Clinical Development," *Cancer Biol. Ther.* S1:S5-S15.
Alley et al. (1988) "Feasibility of Drug Screening with Panels of Human Tumor Cell Lines Using a Microculture Tetrazolium Assay," *Cancer Res.* 48:589-601.
Anderson et al. (1995) "Systemic Treatment for Advanced Cutaneous Melanoma," *Oncology* 9:1149-1154.
Arbuzov et al. (1962) "Reaction of Some Substituted Triarylhalomethanes with Salts of Dialkyl Phosphates. III. Reaction of Crystalline Triphenylchloromethane with Sodium Diethyl Phosphates," *Izvestiya Akademii Nauk SSSR, Seriya Khimichekaya* 11:1945-1946 Abstract Only.
Arbuzov et al. (1962) "Reaction of Some Substitutes Triarylchloro- and -Bromo-Methanes with Salts of Dialkyl Phosphates," *Doklady Akademii Nauk SSSR* 144:1039-1041 Abstract Only.
Arbuzov et al. (1959) "Action of Halo-Substituted Ethers on Salts of Dialkyl Phosphites," *Izvestiya Akademii Nauk SSSR, Seriya Khimicheskaya* :35-40 Abstract Only.
Bhattacharya et al. (1981) "The Michaelis-Arbuzov Rearrangement," *Chem. Rev.* 81(4):415-430.
Blake et al. (1997) "Estrogen can Protect Splenocytes from the Toxic Effects of the Environmental Pollutant 4-*tert*-Pctylphenol," *Endocrine* 6(3):243-249.
Blatt et al. (2001) "Signaling Pathways and Effector Mechanisms Pre-Programmed Cell Death," *Bioorg. Med. Chem. Lett.* 9:1371-1384.
Boisselle et al. (1962) "Acetylene-Allene Rearrangements. Reactions of Trivalent Phosphorus Chlorides with α-Acetylenic Alcohols and Glycols," *J. Org. Chem.* 27(5):1828-1833.
Boyd et al. (1995) "Some Practical Considerations and Applications of the National Cancer Institute in Vitro Anticancer Drug Discovery Screen," *Drug Dev. Res.* 34:91-109.
Bundgaard, H. (1985) "Design of Prodrugs," *Methods Enzymol.* 42:309-396.
Bundgaard, H. (1991) "Design and Application of Prodrugs," In; *A Textbook of Drug Design and Development*, Krosgaard et al. eds., pp. 113-191.
Bundgaard , H. (1992) "(C)Means to Enhance Penetration: (1) Prodrugs as a Means to Improve the Delivery of Peptide Drugs," *Adv. Drug Deliv. Rev.* 8:1-38.

(Continued)

*Primary Examiner*—Rei-tsang Shiao
(74) *Attorney, Agent, or Firm*—Greenlee, Winner and Sullivan, P.C.

(57) ABSTRACT

Compounds and related methods for synthesis, and the use of compounds and combination therapies for the treatment of cancer and modulation of apoptosis in cells are disclosed. Particularly disclosed are phosphonate esters. Compounds, methods of making the compounds, medicaments and method of manufacture of medicaments and therapeutic methods with applications against cancer including breast cancer, melanoma, colon cancer, leukemia and lymphoma, and other cancer cells are described.

47 Claims, 4 Drawing Sheets

OTHER PUBLICATIONS

Cannon-Albright et al. (1992) "Assignment of a Locus for Familial Melanoma, MLM, to Chromosome 9p13-p22," *Science* 258:1148-1152.

Cossarizza et al. (2001) "Analysis of Mitochondria During Cell Death," *Methods Cell Biol.* 63:467-486.

de Graaff et al. (1999) "In Vitro Antagonistic Cytotoxic Interactions Between Platinum Drugs and Taxanes on Bone Marrow Progenitor Cell CFU-GM," *Anticancer Drugs* 10:213-218.

Dothager et al. (Jun. 2005) "Synthesis and Identification of Small Molecules that Potently Induce Apoptosis in Melanoma Cells Through G1 Cell Cycle Arrest," *J. Am. Chem. Soc.* 127(24):8686-8696.

Fountain et al. (1992) "Homozygous Deletions within Human Chromosome Band 9p21 in Melanoma," *Proc. Nat. Acad. Sci. USA* 89:10557-10561.

Gallagher et al. (Sep. 1979) "Characterization of the Continuous, Differentiating Myeloid Cell Line (HL-60) from a Patient with Acute Promyelocytic Leukemia," *Blood* 54(3):713-733.

Goode et al. (Aug. 2005) "Using Peptidic Inhibitors to Systematically Probe the S1' Site of Caspase-3 and Caspase-7," *Org. Lett.* 7(16):3529-3532.

Gramstad et al. (1977) "Studies of Hydrogen Bonding. Part XXVIII. Hydrogen Bond Association of Phenol with 5,5-dimethyl-2-oxo-1,3,2-Dioxaphosphorinanes and Diethylphosphonates," *Acta. Chemica Scand. B. Org. Chem. Biochem.* B31(5):345-353.

Grever et al. (1992) "The National Cancer Institute: Cancer Drug Discovery and Development Program," *Sem. Oncol.* 19(6):622-638.

Grossman et al. (1999) "Expression and Targeting of the Apoptosis Inhibitor, Survivin, in Human Melanoma," *J. Invest. Dermatol.* 113:1076-1081.

Hanahan et al. (2000) "The Hallmarks of Cancer," *Cell* 100:57-70.

Hartmann et al. (2000) "Caspase-3: A Vulnerability Factor and Final Effector in Apoptotic Death of Dopaminergic Neurons in Parkinson's Disease," *Proc. Nat. Acad. Sci. USA* 97:2875-2880.

Haskell et al. (1980) "Melphalan," *Cancer Treatment*, 1st edition, W.B. Saunders Company pp. 62-87.

Haskell et al. (1991) "Dactinomycin," *Cancer Treatment*, 3rd edition, W.B. Saunders Company pp. 62-87.

Haskell et al. (2001) "Antineoplastic Agents," *Cancer Treatment*, 5th edition, W.B. Saunders Company pp. 78-87.

Hatt et al. (1933) "The Constitution of Some Phosphorus Derivatives of Triphenylmethane," *J. Chem. Soc.* :776-786.

Helmbach et al. (2001) "Drug-Resistance in Human Melanoma," *Int. J. Cancer* 93:617-622.

Hergenrother, P.J. (2006) "Obtaining and Screening Compound Collections: A User's Guide and a Call to Chemists," *Curr. Opin. Chem. Biol.* :16677847.

Hornung et al. (1997) "CH-πEffect in Dinuclear Antimony(V) Complexes with Bridging Phosphonato Ligands," *Main Group Metal Chem.* 20(3):157-167.

Huang et al. (Oct. 2002) "The Chemical Biology of Apoptosis: Exploring Protein-Protein Interactions and the Life and Death of Cells with Small Molecules," *Chem. Biol.* 9(10):1059-1072.

Hwang et al. (2003) "N-phenethyl-2-phenylacetamide Isolated from *Xenorhabdus nematophilus* Induces Apoptosis Through Caspase Activation and Calpain-Mediated Bax Cleavage in U937 Cells," *Int. J. Oncol.* 22:151-157.

Iliopulos et al. (1965) "Bis-(p-hydroxyphenyl)-alkanphosphonsäureester und davon abgeleitete Polycarbonate," *Angew. Chem.* 77:618-619 (German).

International Search Report Corresponding to International Application No. PCT/US04/35746, Mailed Jul. 22, 2005.

International Search Report, Corresponding to International Application No. PCT/US/07/69307, Mailed on Jan. 10, 2008.

Jemal et al. (May 2002) "Cancer Statistics," *CA Cancer J. Clin.* 52:23-47.

Jeong et al. (2000) "Aromatase Inhibitors from *Lsodon excisus* var. *coreanus*."

Johnstone et al. (Jan. 2002) "Apoptosis: A Link Between Cancer Genetics and Chemotherapy," *Cell* 108:153-164.

Kers et al. (1997) "Aryl H-Phosphonates. 7. Studies on the Formation of Phosphorus-Carbon Bond in the Reaction of Trityl and Benzyl Halides with Dialkyl and diphenyl H-Phosphonates," *Tetrahedron* 53(37):12691-12698.

Khan et al. (2003) "Three Tyrosinase Inhibitors and Antioxidant Compounds from *Salsola foetida*," *Helvetica Chimica Acta* 86:457-464.

Konstantinov et al. (1998) "Alkylphosphocholines: Effects on Human Leukemic Cell Lines and Normal Bone Marrow Cells," *Int. J. Cancer* 77:778-786.

Kopel'tsiv et al. (1986) "Phosphorylation of Methylenequinones. IV. Reaction of Fuchsone and Naphthofuchsone with di- and trialkyl Phosphates," *Zhurnal Obshchei Khimii* 56(3):588-592.

Kunishima et al. (2001) "Formation of Carboxamides by Direct Condensation of Carboxylic Acids and Amines in Alcohols Using a New Alcohol- and Water- Soluble Condensing Agent: DMT-MM," *Tetrahedron* 47:1551-1558.

Kunishima et al. (2002) "Approach to Green Chemistry of DMT0MM: Recovery and Recycle of Coproduct to Chloromwethane-Free DMT-MM," *Tetrahedron. Lett.* 43:3323-3326.

Lee et al. (2001) "Two New Constituents of *Isodon excisus* and Their Evaluation in an Apoptosis Inhibition Assay," *J. Nat. Prod.* 64:659-660.

Lee et al. (2002) "Agastinol and Agastenol, Novel Ligans from *Agastache rugosa* and Their Evaluation in a Apoptosis Inhibition Assay," *J. Nat. Prod.* 65:414-416.

Lev et al. (2004) "Exposure of Melanoma Cells to Dacarbazine Results in Enhanced Tumor Growth and Metastasis in Vivo," *J. Clin. Oncol.* 22:2092-2100.

Li et al. (2000) "Immunotoxicity of N,N-Diethylaniline in Mice: Effect on Natural Killer Activity, Cytotoxic T Lymphocyte Activity, Lymphocyte Proliferation Response and Cellular Components of the Spleen," *Toxicology* 150:179-789.

LoRusso et al. (1999) "Preclinical Antitumor Activity of XK469 (NSC 656889)," *Invest. New Drugs* 16:287-296.

Makin et al. (Jun. 2003) "Recent Advances in Understanding Apoptosis: New Therapeutic Opportunities in Cancer Chemotherapy," *Trends Mol. Med.* 9(6):251-255.

Malatesta, P. (1963) "Phosphoric Acid Esters with High Anticholinesterase Activity. II Paroxon Analogs," *Farmaco, Edizione Scientifica* 18(10):714-720.

Marx, J. (Sep. 2001) "New Leads on the 'How' of Alzheimer's," *Science* 293:2192-2194.

Mattson et al. (Nov. 2000) "Apoptosis in Neurodegenerative Disorders," *Nat. Rev. Mol. Cell Biol.* 1:120-129.

McGovern et al. (1985) "Pathology of Melanoma: An Overview," In; *Cutaneous Melanoma: Clinical Management and Treatment Results Worldwide*, Chapter 3, J.B. Loppincott Co., Philadelphia, pp. 29-53.

Middleton et al. (2000) "A Randomized Phase III Study Comparing Dacarbazine, BCNU, Cisplatin and Tamoxifen with Dacarbazine and Interferon in Advanced Melanoma," *Br. J. Cancer* 82:1158-1162.

Miganu et al. (2005) "New Efficient Synthesis of 1-Hydroxymethylene-1, 1-Bisphosphonate Monomethyl Esters," *Synlett* 3:425-428.

Min et al. (1989) "Photolysis of triphenylmethylphosphonic Acid and its Dimethyl Esters: A Novel Photochemical Generation of Dimethoxyphosphinyl(phenyl)carbine by α,α-Elimination of Phenyl Groups," *J. Chem. Soc. Chem. Commun.* 3:151-153.

Monks et al. (Oct. 1997) "The NCI Anti-Cancer Drug Screen: A Smart Screen to Identify Effectors of Novel Targets," *Anti-Cancer Drug Design* 12(7):533-541.

Mühlenbeck et al. (1996) "Formation of Hydroxycinnamoylamides and α-Hydroxyacetovanillone in Cell Cultures of *Solanum khasianum*," *Phytochemistry* 42(6):1573-1579.

Negrel et al. (1996) "Ether-Linked Ferulic Acid Amides in Natural and Wound Periderms of Potato Tuber," *Phytochemistry* 43(6):1195-1199.

Nesterenko et al. (2003) "Identification from a Combinatorial Library of Small Molecule that Selectively Induces Apoptosis in Cancer Cells," *J. Am. Chem. Soc.* 125(48):14672-14673.

Nesterenko et al. (2003) "The Use of pH to Influence Regio- and Chemoselectivity in the Asymmetric Aminohydroxylation of Styrenes," *J. Org. Lett.* 5(3):281-284.

Newmeyer et al. (Feb. 2003) "Mitochondria: Releasing Power for Life and Unleashing the Machineries of Death," *Cell* 112:481-490.

Nguyen et al. (Jun. 2003) "Direct Activation of the Apoptosis Machinery as a Mechanism to Target Cancer Cells," *Proc. Nat. Acad. Sci. USA* 100(13):7533-7538.

Nielsen et al. (Apr. 1988) "Glycoamide Esters as Biolabile Prodrugs of Carboxylic Acid Agents: Synthesis, Stability, Bioconversion, and Physicochemical Properties," *J. Pharm. Sci.* 77(4):285-298.

Nogrady (1985) "Pro-drugs and Soft drugs," *Medicinal Chemistry A Biochemical*.

Oredipe et al. (2003) "Limits of Stimulation of Proliferation and Differentiation of Bone Marrow Cells of Mice Treated with Swainsonine," *Int. Immunopharm.* 3:1537-1547.

Plowman, J. (Feb. 1995) "Efficacy of the Quinocarmycins KW2152 and DX-52-1 Against Human Melanoma Lines Growing in Culture and in Mice," *Cancer Res.* 55(4):862-867.

Prater et al. (2002) "Single-Dose Topical Exposure to the Pyrethroid Insecticide, Permethrin in C57BL/6N Mice: Effect on Thymus and Spleen," *Food Chem. Toxicol.* 40:1863-1873.

Promega Technical Bulletin #TB169, "CellTirer96 AQ$_{ueous}$ Non-Radioactive Cell Proliferation Assay," Apr. 2005.

Putt et al. (Jan. 2005) "Direct Quantitation of Poly(ADP-Ribose) Polymerase (PARP) Activity as a Means to Distinguish Necrotic and Apoptotic Death in Cell and Tissue Samples," *Chembiochem.* 6(1):53-55.

Putt et al. (2004) "A Nonradiometric, High-Throughput Assay for Poly(ADP-Robose) Glycohydrase (PARG): Application to Inhibitor Identification and Evaluation," *Anal. Biochem.* 333(2):256-264.

Putt et al. (Mar. 2004) "An Enzymatic Assay for Poly(ADP-Ribose) Polymerase-1 (PARP-1) via the Chemical Quantitation of NAD(+): Application to the High-Throughput Screening of Small Molecules as Potential Inhibitors," *Anal Biochem.* 326(1):78-86.

Reed, J.C. (Feb. 2002) "Apoptosis Based Therapies," *Nat. Rev. Drug Dis.* 1:111-121.

Satyamoorthy et al. (2001) "No Longer a Molecular Black Box—New Clues to Apoptosis and Drug Resistance in Melanoma," *Trends Mol. Med.* 7:191-194.

Schadendorf et al. (1994)"Chemosensitivity Testing of Human Malignant Melanoma. A Retrospective Analysis of Clinical Response and In Vitro Drug Sensitivity," *Cancer* 73:103-108.

Serrone et al. (2000) "Dacarbazine-Based Chemotherapy for Metastic Melanoma: Thirty-Year Experience Overview," *J. Exp. Clin. Cancer Res.* 19:21-34.

Shermolovich et al. (1980) "Reactions of Fuchsone with Dialkyl Hydrogen and Trialkyl Phosphites," *J. Gen. Chem. USSR* 50(4):649-652 (Translated from *Zokha4 Zh. Obshch. Khim.* 51(4):811-815) Abstract Only.

Shi et al. (1990) "Photolysis of (truarylmethyl)phosphonic Acids and Their Esters," *Bull. Chem. Soc. Jpn.* 63(2):453-460.

Shi et al. (1990) "Photolysis of Diaryl Triphenylmethylphosphonates," *Bull. Chem. Soc. Pn.* 63(4):1269-1271.

Silverman et al. (May 2006) "Combinatorial Chemistry and Molecular Diversity Tools for Molecular Diversification and Their Application in Chemical Biology," *Curr. Opin. Chem. Biol.* :16675287.

Soengas et al. (2003) "Apoptosis and Melanoma Chemoresistance," *Oncogene* 22:3138-3151.

Soengas et al. (2001) "Inactivation of the Apoptosis Effector Apaf-1 in Malignant Melanoma," *Nature* 409:207-211.

Sundstrom et al. (1976) "Establishment and Characterization of a Human Histiocytic Lymphoma Cell Line (U-937)," *Int. J. Cancer.* 17:565-577.

Vichai et al. (2006) "Sulforhodamine B Colorimetric Assay for Cytotoxicity Screening," *Nature Protocols* 1(3):1112-1116.

Wilen et al. (1977) "Strategies in Optical Resolutions," *Tetrahedron* 33(21):2725-2736.

Witt et al. (1996) "Reactivity of the Acids of Trivalent Phosphorus and Their Derivatives. Part VIII. Reactivity of the >P-O-Nucleophiles Toward Arylmethyl Bromide Systems. Further Evidence for the X-philic Substitution/SET Tandem Mechanism," *Phosphorus Sulfur Silicon Related Elements* 117:149-165.

Yamaura et al. (Feb. 2002) "Inhibition of the Antibody Production by Acetaminophen Independent of Liver Injury in Mice," *Biol. Pharm. Bull.* 25:201-205.

Young et al. (1956) "The Use of Phosphorus Acid Chlorides in Peptide Synthesis," *J. Am. Chem. Soc.* 78(10):2126-2131.

Zhou et al. (1998) "Reactions of 4-alkyl-1-trityl-1-phospha-2,6,7-trioxabicyclo[2.2.2]octane Cations with Bases," *Phosphorus Sulfur Silicon Related Elements* 132:183-206.

Johansson et al. (2002) "Studies on the Synthesis of Picolylphosphonare Diesters," *Collection Symp. Series, 5 Chemistry of Nucleic Acids Components* :81-86.

* cited by examiner

PHOSPHOROUS CONTAINING COMPOUNDS INCLUDING TRIPHENYLMETHYLPHOSPHONATE ESTERS FOR THE TREATMENT OF MELANOMA AND OTHER CANCERS

CROSS-REFERENCES TO RELATED APPLICATIONS

This application claims the benefit of U.S. provisional application 60/747,747, filed May 19, 2006 which is incorporated by reference herein in its entirety.

STATEMENT ON FEDERALLY SPONSORED RESEARCH OR DEVELOPMENT

Not Applicable

BACKGROUND OF THE INVENTION

Cancer is a multifaceted disease that strikes millions every year. As there are many varieties of normally differentiated cell types, there is a large proportion of abnormalities that become clinically important in humans and animals. For example, melanoma is a particularly devastating type of cancer with a five-year survival rate projected to be less than 5%. There is only one single-agent drug approved for the treatment of melanoma; its rate of effectiveness is estimated at as low as about 10%.

In contrast, the onset of certain cancers has been traced to a missed apoptotic signal (Johnstone, R. W.; Ruefli, A. A.; Lowe, S. W. Cell 2002, 108, 153-164). In these cases, compounds that induce apoptosis (such as etoposide, doxorubicin, and camptothecin) have proven to be powerful chemotherapeutic agents. However, for a compound to be medicinally useful it is critical that this apoptotic induction be selective for cancer versus non-cancer cells. Indeed, it is rare to find compounds that have the selectivity needed to merit serious consideration as chemotherapeutic agents (Haskell, C. M. Cancer Treatment Ed.; W. B. Saunders Company, 62-87).

Apoptosis, or programmed cell death, is a highly conserved process used by multi-cellular organisms to rid themselves of unwanted or damaged cells (Blatt, N. B., Glick, G. D. Bioorg. Med. Chem. Lett. 2001, 9, 1371-1384; Newmeyer, D. D.; Ferguson-Miller, S. Cell 2003, 112, 481-490; Huang, Z. Chem. Biol. 2002, 9, 1059-1072). Hallmarks of apoptosis include cellular membrane blebbing, cleavage of certain nucleases and polymerases, and activation of cysteine proteases known as caspases. From a medicinal perspective, small molecules that either inhibit or induce apoptosis have significant therapeutic potential (Reed, J. C. Nat. Rev. Drug Dis. 2002, 1, 111-121; Makin, G.; Dive, C. Trends Mol. Med. 2003, 9, 251-255). Besides cancer, degenerative disorders such as Alzheimer's and Parkinson's diseases are thought to result from an aberrant increase in apoptosis (Hartmann, A. et al. Proc. Natl. Acad. Sci. 2000, 97, 2875-2880; Mattson, M. P. Nat. Rev. Mol. Cell. Biol. 2000, 1, 120-129; Marx, J. Science 2001, 293, 2192-2194). In such cases, apoptotic inhibitors hold considerable medicinal promise.

Clearly there is a tremendous need to develop compositions and methods better able to address cancers. The identification of chemically-based libraries of compounds, individual compounds, combinations of compounds, and methods for applications in the treatment and study of cancer and the modulation of apoptosis are of significant value.

U.S. Pat. Nos. 3,847,866 and 3,702,879 (both by Bredereck, Iliopulos and Wieder) may describe certain phosphonate ester compounds. The invention in part relates to triphenylmethylphosphonate ester compounds and methods of making and using thereof in the surprising context of applications to cancer cells.

SUMMARY OF THE INVENTION

The invention provides compounds and related methods for apoptosis modulation and the treatment of cancer cells. The invention also provides methods for combination therapies wherein compounds of the invention are used with one or more chemotherapeutic agents.

Without wishing to be bound by a particular theory, it is believed that compounds of the invention may act via the mechanism of modulation of apoptosis or programmed cell death to be effective in the treatment of cancer cells. It is envisioned that compounds and methods of the invention can be effective in the treatment of cancer without necessarily involving the mechanism of apoptosis. In a preferred embodiment, the modulation of apoptosis is by induction of apoptosis. In another embodiment, the modulation of apoptosis is by inhibition of apoptosis.

In an embodiment, a compound of the invention is an inducer of cell death in a cancer cell. In another embodiment, a compound herein is an inducer of cell death in a plurality of cancer cells. In an embodiment, induction of cell death occurs in vitro, in vivo, or ex vivo. In an embodiment, a compound of the invention is capable of regulating cell development, differentiation, and/or viability.

In a particular embodiment, a compound of the invention is an inducer of cell death in at least one of a lymphoma cell, leukemia cell, non-small cell lung cancer cell, colon cancer cell, brain or central nervous system (CNS) cancer cell, melanoma cell, ovarian cancer cell, renal cancer cell, prostate cancer cell, and breast cancer cell.

In a particular embodiment, a compound of the invention is an inducer of cell death in a lymphoma. In a particular embodiment, a compound of the invention is an inducer of cell death in a leukemia cell. In a particular embodiment, a compound is of the invention an inducer of cell death in a melanoma cell. In a particular embodiment, a compound of the invention is an inducer of cell death in a breast cancer cell. In a particular embodiment, a compound of the invention is an inducer of cell death in a cell type of a screening panel of 60 members used by the National Cancer Institute.

In an embodiment, a compound or library of the invention is useful in screening to identify a compound having activity against a cancer cell.

This invention broadly relates to chemical compositions including compounds described generally as phosphonate esters and those described as phosphonochloridic acids, and particularly those which contain optionally substituted triphenylmethyl groups. Such compounds of the invention are useful, for example, for induction of cell death. In particular embodiments of the invention, the induction of cell death occurs via apoptosis. The compounds of the invention are also useful for therapeutic benefit in the clinical treatment of cancer. Compounds of the invention are also useful in particular for therapeutic benefit in the clinical treatment of cancers that are highly metastatic, including melanoma. Certain compounds of the invention have been tested in one or more cancer cell lines and can exhibit selective ability to kill cancer cells.

Phosphonate esters of this invention include those of formula FX1:

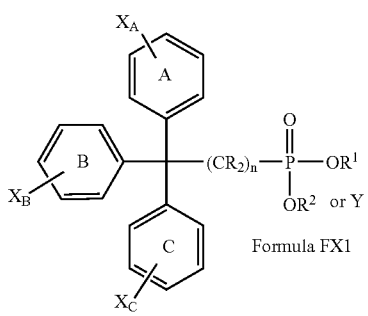

Formula FX1 wherein:

Aryl rings A, B and C, independently of one another, are selected from the group consisting of phenyl rings or six-member aromatic rings where one or two carbon atoms are replaced with nitrogens and which are optionally substituted on one or more ring carbons;

$X_A$, $X_B$, $X_C$ represent one or more hydrogens or non-hydrogen ring substituents independently selected from the group consisting of halogens, hydroxides, alkyl, alkenyl, alkynyl, alkoxide, thiol, thioalkoxide, ether, thioether, nitro, cyano, isocyano, cyanato, isocyanato, thiocyano, isothiocyano, amine (—N(R')$_2$), R'—CO—, R'O—CO—, (R')$_2$N—CO—, $R_{10}$—COO—, (R')$_2$N—COO—, (R')$_2$N—CONR', R'SO$_2$—, R'$_2$NSO$_2$— groups, wherein carbon atoms of these substituent groups are optionally substituted with one or more halogens, hydroxides, thiols, nitro groups, cyano groups, isocyano groups, cyanato groups, isocyanato groups, thiocyanato groups, or isothiocyano groups, wherein R', independent of other R' in the molecule, are selected from H, alkyl, alkenyl, alkynyl, heterocyclic, aryl, heteroaryl, all of which can in turn be optionally substituted with one or more halogens, hydroxides, alkyl, alkenyl, alkynyl, alkoxide, thiol, thioalkoxide, ether, thioether, nitro, cyano, isocyano, cyanato, isocyanato, thiocyano, isothiocyano, amine (—N(R')$_2$), R"CO—, R"O—CO—, (R")$_2$N—CO—, R"O—COO—, (R")$_2$N—COO—, (R")$_2$N—CONR", R"SO$_2$—, or R"$_2$NSO$_2$— groups, where R", independently of other R" in the molecule, are selected from the group consisting of hydrogen, alkyl, alkenyl, alkynyl, heterocyclic, aryl, or heteroaryl groups optionally substituted with one or more halogens, alkyls, alkenyls, alkynyls, aryls, hydroxides, thiols, nitro groups, cyano groups, isocyano groups, cyanato groups, isocyanato groups, thiocyanato groups, or isothiocyano groups;

$X_A$, $X_B$, $X_C$ substitution on the A, B and C rings can also include a linking moiety between two of the aryl rings, wherein the linking moiety can be a —O—, —S—, —NH—, or —CR$_2$'"— moiety wherein each R'", independently of any other R'", is selected from the group consisting of H or alkyl groups having 1-6 carbon atoms;

OR$^2$ is optionally replaced with Y which is a halogen, preferably chloride or fluoride;

R$^1$ and R$^2$, independently of one another, are selected from the group consisting of alkyl, alkenyl, alkynyl, ether, thioether, heterocyclic, aryl or heteroaryl groups which are optionally substituted with one or more halogens, hydroxides, alkyl, alkenyl, alkynyl, alkoxide, thiol, thioalkoxide, ether, thioether, amine (—N(R')$_2$), nitro, cyano, isocyano, cyanato, isocyanato, thiocyano, isothiocyano, R'—CO—, R'O—CO—, (R')$_2$N—CO—, R'O—COO—, (R')$_2$N—COO—, (R')$_2$N—CONR', R'SO$_2$—, or R'$_2$NSO$_2$— group, where R' is as defined above and wherein R$^1$ and R$^2$ together can form an optionally substituted alkylene or alkenylene group having 2 or more carbon atoms bonded between the two oxygens in formula FX1 which are in turn bonded to phosphorous (here the "two oxygens" refers to the oxygen atoms connected to phosphorous by a single bond);

each R, independent of other R in the molecule, are selected from the group consisting of hydrogen, hydroxide, halogen, alkyl, alkoxide wherein carbon atoms of these substituent groups are optionally substituted with one or more halogens, hydroxides, thiols, nitro groups, cyano groups, isocyano groups, cyanato groups, isocyanato groups, thiocyanato groups, or isothiocyano groups;

and n is 0, 1, 2, 3, 4, 5 or 6.

In an embodiment of formula FX1, all of the A, B and C aryl rings are phenyl rings and the compounds contain optionally substituted triphenylmethyl groups. In an embodiment of FX1, $R_2$ is H, and therefore $(CR_2)_n$ is $(CH_2)_n$. In an embodiment of FX1, n is 0 so (CR$_2$) is absent. In an embodiment of FX1, all of the A, B and C aryl rings are phenyl rings and n is 0 and the compounds are optionally substituted triphenylmethylphosphonates.

In specific embodiments —OR$^2$ is replaced with Y in formula FX1 and Y is a halogen and in particular Y is F or Cl.

In specific embodiments where the $X_A$, $X_B$, $X_C$ substitution on the A, B and C rings can also include a linking moiety between two of the aryl rings, the linking moiety is —O—.

In more specific embodiments, the invention provides compounds of formula FX3C:

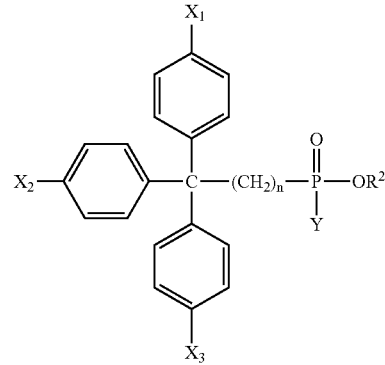

wherein:
Y is or OR$^1$;
n is 0 or 1;
R$^1$ and R$^2$, independently of one another, are selected from the group consisting of unsubstituted alkyl, alkenyl or alkynyl groups having 1 to 6 carbon atoms;
$X_1$, $X_2$ and $X_3$, independently of one another, are H, alkyl groups having 1-6 carbon atoms or alkoxide groups having 1-6 carbon atoms.

In specific embodiments of FX3C, Y is chlorine and n is 0. In other specific embodiments, Y is OR$^1$ and n is 0.

In specific embodiments of FX3C, R$^1$ and R$^2$ are alkenyl groups having 2-6 carbon atoms or alkynyl groups having 2-6 carbon atoms. In additional embodiments, R$^1$ and R$^2$ are alkenyl groups having 2-6 carbon atoms or alkynyl groups having 2-6 carbon atoms and $X_1$, $X_2$ and $X_3$ are hydrogens or alkoxy groups having 1-3 carbon atoms. In additional embodiments, R$^1$ and R$^2$ are alkenyl groups having 2-6 carbon atoms or alkynyl groups having 2-6 carbon atoms and $X_1$, $X_2$ and $X_3$ are hydrogens or methoxy groups.

In specific embodiments of FX3C, Y is chlorine and $R^2$ is an alkenyl group having 2-6 carbon atoms or an alkynyl group having 2-6 carbon atoms. In additional embodiments, Y is chlorine and $R^1$ is an alkenyl group having 2-6 carbon atoms or an alkynyl group having 2-6 carbon atoms and $X_1$, $X_2$ and $X_3$ are hydrogens or alkoxy groups having 1-3 carbon atoms. In additional embodiments, Y is chlorine and $R^1$ is an alkenyl group having 2-6 carbon atoms or an alkynyl group having 2-6 carbon atoms and $X_1$, $X_2$ and $X_3$ are hydrogens or methoxy groups.

In specific embodiments of FX3C, $R^1$ and/or $R^2$ are propyl, butyl, pentyl or hexyl groups including all isomers thereof. In more specific embodiments of FX3C, $R^1$ and/or $R^2$ are n-propyl, iso-propyl, n-butyl, 1-methylpropyl, 2-methylpropyl, n-pentyl, 1-methylbutyl, 2-methylbutyl, 3-methylbutyl, 1-ethylpropyl, n-hexyl, 1-methylpentyl, 2-methylpentyl, 3-methylpentyl, 1-ethylbutyl, 2-ethylbutyl, 3-ethylbutyl, 1,2-dimethylbutyl, 2,3-dimethylbutyl, 1,1-dimethylbutyl, 2,2-dimethylbutyl or 3,3-dimethyl butyl groups. In specific embodiments, $R^1$ and/or $R^2$ are groups other than methyl, ethyl, iso-propyl or neopentyl groups.

In specific embodiments of the compounds herein, $R^1$ and/or $R^2$ are groups other than methyl, ethyl, iso-propyl or neopentyl groups. In specific embodiments of the compounds herein, when $R^1$ is a methyl, ethyl, iso-propyl or neopentyl group, Y is a halogen, particularly a chlorine. In specific embodiments herein when both of $R^1$ or $R^2$ are methyl, ethyl, iso-propyl or neopentyl groups, at least one of $X_1$, $X_2$ or $X_3$ is a substituent other than H, OH or $OCH_3$. In specific embodiments of the compounds herein, when both of $R^1$ and $R^2$ are alkyl groups, at least one of $X_1$, $X_2$ or $X_3$ is a substituent other than H, OH or $OCH_3$.

In specific embodiments, the invention provides compounds of formulas FX2, FX2A, FX2B, FX3, FX3A, FX3B, FX3C, FX3D, FX4, FX4A, FX5, FX5A, FX5B, FX5C and/or one or more compounds of Scheme 1. In specific embodiments, the invention provides novel compounds of any of the formulas herein.

In a specific embodiment, the invention provides pharmaceutical compositions. In an embodiment, a pharmaceutical composition comprises a compound which provides therapeutic benefit wherein the compound is selected from: one or more compounds of formulas described herein, specifically formulas FX1, FX2, FX2A, FX2B, FX3, FX3A, FX3B, FX3C, FX3D, FX4, FX4A, FX5, FX5A, FX5B, FX5C and/or one or more compounds of Scheme 1. A pharmaceutical composition can further comprise one or more of a carrier, excipient, buffer, etc. as would be understood in the art. In specific embodiments, the pharmaceutically acceptable carrier is a carrier other than water or an aqueous solution. The invention further provides pharmaceutical compositions comprising a pharmaceutically acceptable carrier, etc., and one or more compounds of the invention present in the composition in an amount or combined amount that provides a desired therapeutic benefit. The invention provides pharmaceutical compositions comprising a compound described herein dissolved in an aqueous formulation. In an embodiment, a pharmaceutical composition comprises an effective amount, as defined herein, of a compound of the invention.

The invention provides compounds, as described herein, for use in medical therapy. Such therapy can include, for example, use in inducing apoptosis, modulating caspase activity, inducing cell death, or treating cancer, preferably for use in treating lung cancer, breast cancer, prostate cancer, other forms of cancer, lymphoma, and leukemia, such as, for example, acute lymphocytic leukemia (ALL), acute myelogenous leukemia (AML), chronic myelogenous leukemia (CML), and other diseases of proliferation. Such therapy can include as well the use of such compounds for the manufacture of a medicament for inducing apoptosis, modulating caspase activity, inducing cell death, or treating cancer, preferably for use in treating lung cancer, breast cancer, prostate cancer, CML, ALL, AML, other forms of cancer or leukemia, and other diseases of proliferation, in a mammal, such as a human. The compounds of the invention are also useful for treatment in diseases in which apoptosis is one of the symptoms, such as, for example, heart conditions, Parkinson's disease, Alzheimer's disease and the like.

The invention provides methods to induce apoptosis or death in a cell comprising contacting the cell in vivo, ex vivo, or in vitro, with an effective amount of a compound of the invention as described herein. In a preferred embodiment, a cell to be targeted by a composition or method of the invention can be any type of cancer cell, for example a leukemia cell, lymphoma cell, and cells of various tissue types and at various stages of differentiation.

The invention also provides a method to treat cancer or induce apoptosis in a mammal in need of such treatment comprising administering to the mammal, an effective amount of a compound of the invention as described herein.

In an embodiment, the invention provides a compound of any of formulas FX1, FX2, FX2A, FX2B, FX3, FX3A, FX3B, FX3C, FX3D, FX4, FX4A, FX5, FX5A, FX5B, FX5C capable of achieving a value, known as a 50% inhibitory concentration ($IC_{50}$) in a cytotoxicity assay, wherein such IC50 value is less than 300 µM. In a preferred embodiment, such IC50 value is less than 100 µM. In a more preferred embodiment, such IC50 value is less than 50 µM. In yet more preferred embodiments, such value is less than 20 micromolar. In highly preferred embodiments, such value is less than 10 micromolar and/or less than 1 micromolar. In specific embodiments, IC50 values are determined employing the sulphorhodamine B assay for assessing cell death.

The invention also provides a method to activate a caspase in a cell comprising contacting the cell, in vitro or in vivo, with an effective amount of a compound of the invention as described herein.

The invention also provides a method for preventing or treating a pathological condition or symptom in a mammal, such as a human, associated with caspase (for example, caspase 3) activation comprising administering to a mammal in need of such therapy, an effective caspase-modulating amount of a compound of the invention as described herein.

The invention also provides a therapeutic method to induce cell death comprising contacting a cell, in vivo, ex vivo, or in vitro, with an effective amount of a compound of the invention as described herein. In an embodiment, the induction of cell death is at least partially selective for cancer cells.

The invention also provides a method to induce cell death in a mammal in need of such treatment comprising administering to the mammal, an effective amount of a compound of the invention as described herein.

The invention also provides a method to treat cancer (e.g., lung cancer, breast cancer, prostate cancer, ALL, AML, solid tumors, other forms of cancer or leukemia, and other diseases of proliferation) in a mammal in need of such treatment comprising administering to the mammal, an effective amount of a compound of the invention as described herein.

The invention provides methods of treating a cancer cell comprising contacting said cell with a therapeutically effective amount of a combination of a compound of the invention and a chemotherapeutic agent. In a preferred embodiment, the chemotherapeutic agent is one other than the compound of the present invention. In a specific embodiment, the chemotherapeutic agent that is combined with a compound of this invention is one that acts by a mechanism that is different from that of a compound of the invention. In a specific embodiments, the chemotherapeutic agent that is combined with a compound of this invention is one that acts by causing damage to DNA. In a specific embodiments, the chemotherapeutic agent that is combined with a compound of this invention is one which affect mitosis and ultimately result in G2/M arrest. The invention provides methods of treating cancer in a subject comprising administration of an amount of a chemotherapeutic agent and an amount of a compound of the invention, wherein the combined amounts of chemotherapeutic agent and said compound are effective to treat cancer in the subject. In an embodiment, the agent comprises dacarbazine, etoposide, doxorubicin, camptothecin, or analogs or derivatives thereof or other chemotherapeutic agent. In an embodiment, the components of a combination therapy have an additive effect. In another embodiment, the components of a combination therapy have a synergistic or potentiating effect. In an embodiment, a compound of the invention and a chemotherapeutic agent are administered sequentially, or simultaneously, wherein the administration including the order of components is optionally selected for optimal clinical results.

The invention provides methods for screening a modulating agent which when combined with an anticancer therapeutic agent increases apoptosis in cancer cells. In an embodiment, the modulating agent is a compound of the invention. The invention also provides methods for screening anticancer therapeutic agents suitable for combination therapy with a compound of the invention.

The invention provides methods of generating a chemical library of compounds. In an embodiment, the library is combinatorial.

The invention provides methods for synthesis of compounds of the invention.

In an embodiment, a compound of the invention is provided in purified and/or substantially pure form. In an embodiment, possible prodrugs and pharmaceutical compositions, including possible salts, are provided in connection with compounds of the invention.

Other aspects and embodiments of the inventions will be apparent on consideration of the figures, detailed description and the examples provided herein.

DETAILED DESCRIPTION OF THE INVENTION

Figure 1:
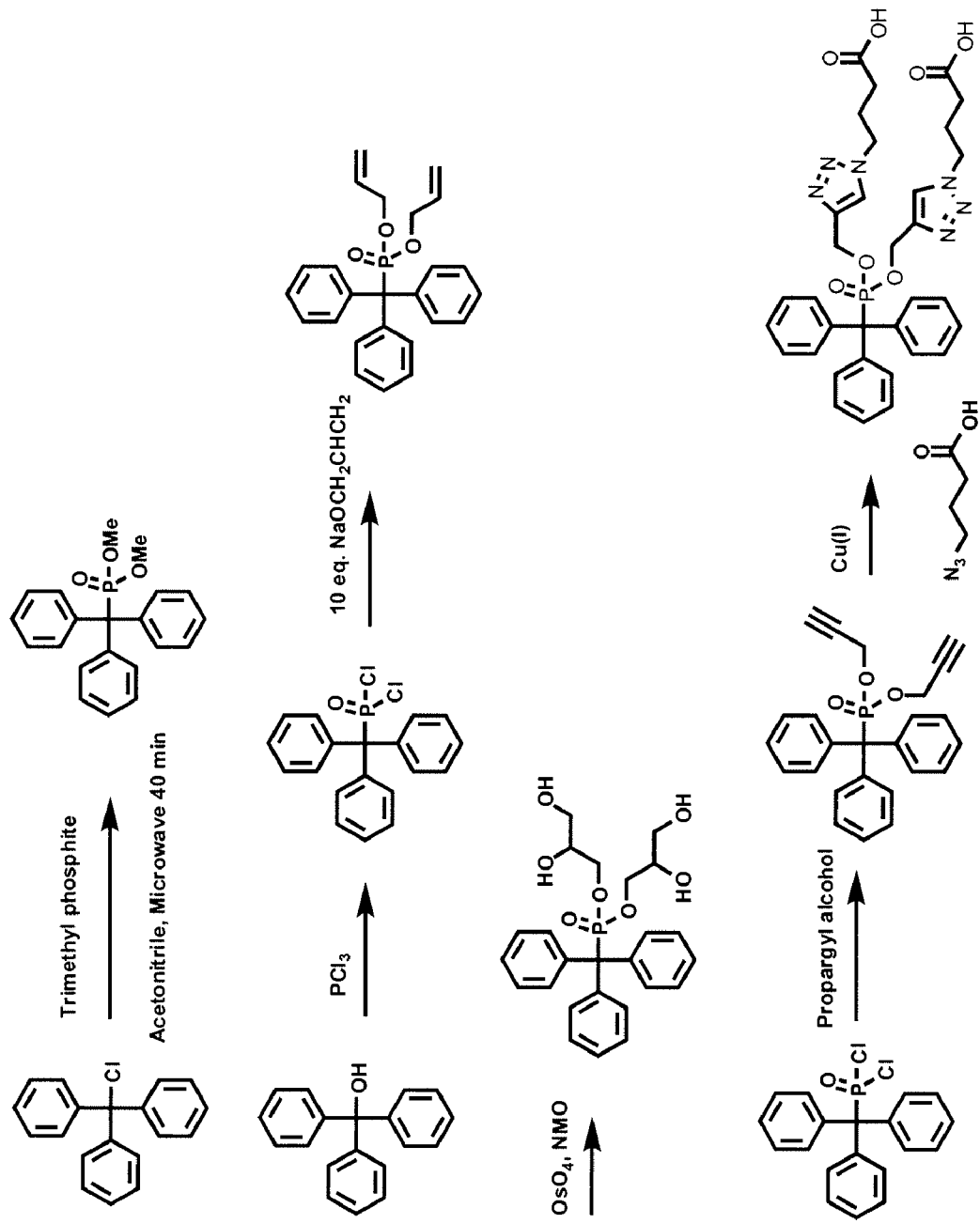
FIG. 1 illustrates methods of synthesis for compounds, including schemes that can be used for synthesis of TPMP compounds of particular potency such as CX1, CX2, and CX4.

In general the terms and phrases used herein have their art-recognized meaning, which can be found by reference to standard texts, journal references and contexts known to those skilled in the art. The following definitions are provided to clarify their specific use in the context of the invention.

The term chemotherapeutic agent herein refers to any substance capable of reducing or preventing the growth, proliferation, or spread of a cancer cell, a population of cancer cells, tumor, or other malignant tissue. The term is intended also to encompass any antitumor or anticancer agent. Exemplary chemotherapeutic agents include among others, cisplatin, etoposide, irinotecan, camptostar, topotecan, paclitaxel, docetaxel, epothilones, taxotere, taxol, tamoxifen, 5-fluorouracil, methoxtrexate, temozolomide, cyclophosphamide, SCH 66336, R115777, L778,123, BMS 214662, IRESSA™. (gefitinib), TARCEVA™. (erlotinib hydrochloride), antibodies to EGFR, GLEEVEC™ (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, Teniposide 17.alpha.-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux™ (cetuximab), Liposomal, Thiotepa, Altretamine, Melphalan, Trastuzumab, Lerozole, Fulvestrant, Exemestane, Fulvestrant, Ifosfomide, Rituximab, C225, and Campath and more generally any art-recognized cytostatic agent. Chemotherapeutic agents include analogs and derivatives of the chemotherapeutic agents specifically listed above which exhibit function for reducing or preventing the growth, proliferation, or spread of a cancer cell, a population of cancer cells, tumor, or other malignant tissue, including, for example, analogs and derivatives of dacarbazine, etoposide, doxorubicin and camptothecin. It will be appreciated by one of ordinary skill in the art and it is intended herein that the term chemotherapeutic agents refers to such agent that are presently art-recognized and also to those agents which will be approved for such uses in the future.

In general, the compounds of this invention can be employed in combination with any art-recognized chemotherapeutic agent. In general, treatment of an individual with any one or more of the compounds of this invention can be combined with any art-recognized chemotherapeutic treatment. In a specific embodiment, one or more compounds of this invention can be employed with one or more chemotherapeutic agents which cause DNA damage, such as, for example, cisplatin, doxorubicin or cyclophosphamide (or analogs or derivatives thereof). In a specific embodiment, one or more compounds of this invention can be employed with one or more chemotherapeutic agents, such as, for example, etoposide, taxol, or cholchicine (or analogs or derivatives thereof).

The term effective amount, when used herein, is intended to encompass contexts such as a pharmaceutically effective amount or therapeutically effective amount. In a particular embodiment, it will be apparent that the context will allow one of ordinary skill to recognize, determine, or establish an effective amount. For example, an effective amount in the context of inducing cell death or otherwise regulating cell development, differentiation, and/or viability will have a functional impact on one or more measurable parameters. A therapeutically effective amount will be understood, for example, to beneficially affect a clinical condition such as the disease of cancer and its progression; such an amount may provide at least temporary and/or partial amelioration of the condition.

The invention provides embodiments of medicaments and methods of making medicaments comprising one or more compounds of the invention. The invention provides compositions comprising one or more compounds for use in the manufacture of medicaments. The invention provides methods of use of one or more compounds of the invention in a cell. In an embodiment such use is in vitro, in vivo, or ex vivo.

When used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art. A cancer cell can be along a continuum or spectrum of development or differentiation and can include an early stage form that is considered precancerous.

The term "alkyl" refers to a monoradical of a branched or unbranched (straight-chain or linear) saturated hydrocarbon and includes cycloalkyl groups having one or more rings. Unless otherwise indicated preferred alkyl groups have 1 to 30 carbon atoms and more preferred are those that contain 1-22 carbon atoms. Short alkyl groups are those having 1 to 6 carbon atoms including methyl, ethyl, propyl, butyl, pentyl and hexyl groups, including all isomers thereof. Long alkyl groups are those having 8-30 carbon atoms and preferably those having 12-22 carbon atoms as well as those having 12-20 and those having 16-18 carbon atoms. The term "cycloalkyl" refers to cyclic alkyl groups having preferably 3 to 30 carbon atoms having a single cyclic ring or multiple rings. Cycloalkyl groups include, by way of example, single ring structures such as cyclopropyl, cyclobutyl, cyclopentyl, cyclooctyl, and the like, or multiple ring structures such as adamantanyl, and the like.

The term "alkenyl" refers to a monoradical of a branched or unbranched unsaturated hydrocarbon group and to cycloalkenyl groups having one or more rings wherein at least one ring contains a double bond. Unless otherwise indicated preferred alkyl groups have 1 to 30 carbon atoms and more preferred are those that contain 1-22 carbon atoms. Alkenyl groups may contain one or more double bonds (C=C) which may be conjugated or unconjugated. Preferred alkenyl groups are those having 1 or 2 double bonds and include omega-alkenyl groups. Short alkenyl groups are those having 2 to 6 carbon atoms including ethylene (vinyl), propylene, butylene, pentylene and hexylene groups, including all isomers thereof. Long alkenyl groups are those having 8-30 carbon atoms and preferably those having 12-22 carbon atoms as well as those having 12-20 carbon atoms and those having 16-18 carbon atoms. The term "cycloalkenyl" refers to cyclic alkenyl groups of from 3 to 30 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl.

The term "alkynyl" refers to a monoradical of an unsaturated hydrocarbon having one or more triple bonds (C≡C). Unless otherwise indicated preferred alkyl groups have 1 to 30 carbon atoms and more preferred are those that contain 1-22 carbon atoms. Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms.

Alkyl, alkenyl, and alkynyl groups may be substituted or unsubstituted. Alkyl, alkenyl, and alkynyl groups may be optionally substituted as described herein and may contain non-hydrogen substituents dependent upon the number of carbon atoms in the group and the degree of unsaturation of the group. Unless otherwise indicated substituted alkyl, alkenyl and alkynyl groups preferably contain 1-10, and more preferably 1-6, and more preferably 1, 2 or 3 non-hydrogen substituents.

The general term hydrocarbon is used herein as it is understood in the art to refer to a compound or group that consists only of the elements carbon (C) and hydrogen (H).

The term alkoxy (or alkoxide) refers to a —O-alkyl group, where alkyl groups are as defined above. The term alkeneoxy (alkenoxide) refers to a —O-alkenyl group where alkenyl groups are as defined above and wherein a double bond is preferably not positioned at the carbon bonded to the oxygen. The term alkyneoxy (alkynoxide) refers to a —O-alkynyl group where alkynyl groups are as defined above and wherein a triple bond is not positioned at the carbon bonded to the oxygen.

The term "alkylene" refers to a diradical of a branched or unbranched saturated hydrocarbon chain, which unless otherwise indicated can have 1 to 10 carbon atoms, or 1-6 carbon atoms, or 2-4 carbon atoms. This term is exemplified by groups such as methylene (—$CH_2$—), ethylene (—$CH_2CH_2$—), more generally —$(CH_2)_n$—, where n is 1-10 or more preferably 1-6 or n is 2, 3 or 4. Alkylene groups may be branched, e.g., by substitution with alkyl group substituents. Alkylene groups may be optionally substituted as described herein. Alkylene groups may have up to two non-hydrogen substituents per carbon atoms. Preferred substituted alkylene groups have 1, 2, 3 or 4 non-hydrogen substituents. Hydroxy-substituted alkylene groups are those substituted with one or more OH groups. Halogen-substituted alkylene groups are those substituted with one or more halogens, e.g., one or more fluorines. The terms "alkenylene" and "alkynylene" refer respectively to a diradical of a branched or unbranched alkene or alkyne. Alkylene, alkenylene and alkynylene groups may from a ring when linked to an atom or between two atoms in a molecule.

The term "heteroalkyl" or "heteroalkylene" in general refers to an alkyl group or alkylene group (i.e., a diradical), respectively, in which one or more $CH_2$, CHR or $CR_2$ moieties (where R is a non-hydrogen substituents) are replaced with O, NR', N, S, P, PR', —$PO_3$— or other non-carbon atoms (i.e., heteroatoms) where R' is hydrogen, or an optionally substituted alkyl, alkenyl, alkynyl or aryl group. The term "heteroalkenyl" and heteteoalkynyl" refer analogously to alkenyl and alkynyl groups, respectively, in which one or more —$CH_2$—, —CHR— or —$CR_2$— moieties (where R is a non-hydrogen substituent) are replaced with a heteroatom. The terms "heteroalkenylene" and "heteroalkynylene" refer to the corresponding diradicals.

The term "heterocyclic" refers generally to a cyclic alkane, alkene, alkyne or aryl compound in which one or more —$CH_2$— (or —CHR— or —$CR_2$—) groups or aryl ring —CH= (or —CR=) groups are replaced with a heteroatom or group of heteroatoms (e.g., —N=, —NR'—, —O—, —S—, —P—, —PR'—, or —$PO_3$—). Exemplary heterocyclic rings are illustrated in the exemplary heterocyclic diradicals Mb-Mp (above). Exemplary heterocyclic monoradicals include those in which one of the open bonds of the Mb-Mp diradicals is bonded to H or a non-hydrogen substituent.

The term "aryl" refers to a radical derived formally by removal of a hydrogen from an aromatic molecule. An aromatic molecule is a molecule that contains at least one aromatic ring, which is typically a 5- or 6-member ring. The term "aromatic" is used as broadly as it is understood in the art. An aromatic ring is typically described as a planar ring (of carbons or heteroatoms) in which 4n+2 pi electron are delocalized over the ring. An aryl group may contain two or more fused aromatic rings which share a pair of carbon or heteroatoms. Aryl groups having at least one heteroatom in the aromatic ring are designated "heteroaryl" groups. Representative examples of aryl groups are benzenes, alkylbenzenes, pyroles, furan, thiophenes, pyridines, pyrimidines, pyridazines, pyrazoles, imidazoles, and pyrazines. Naphthalene (a fused ring aromatic) and quinoline (a fused ring heterocyclic aromatic) are additional examples. The term "arylalkyl" refers to an alkyl group which is substituted with one or more aryl groups. Most generally the alkyl group can carry additional substituents and the aryl group is optionally substituted as described herein, exemplary aryl alkyl groups are triphenylmethyl groups, or a phenyl substituted methyl group. The term "alkylaryl" refers to an aryl group that is substituted with one or more alkyl groups, as exemplified by a methyl substituted phenyl group (e.g., para-methylphenyl group).

The term "arylene" refers to a diradical formally derived by removal of two hydrogens from an aromatic molecule. "Heteroarylene" refers to a diradical formally derived by removal of two hydrogens from a heteroaromatic molecule (a heteroaryl molecule).

The term "ether group" also "alkoxyalkyl" refers to an alkyl group in which one or more —$CH_2$— groups are replaced with —O—. Unless otherwise specified preferred alkoxyalkyl groups have from 3 to 30 carbon atoms and more preferably have 6 to 22 carbon atoms. Ether groups include groups of the formula: —$[(CH_2)_a$—O—$]_b$—$CH_3$ where a is 1-10 and b is 1-6. More specifically, a can be 2, 3 or 4 and b can be 1, 2 or 3. The term "thioether group" or "thioalkoxyalkyl" refers to an alkyl group in which one or more —$CH_2$— groups are replaced with —S—. Unless otherwise specified preferred thioalkoxyalkyl groups have from 3 to 30 carbon atoms and more preferably have 6 to 22 carbon atoms. Thioalkoxylalkyl groups include groups of the formula: —$[(CH_2)_a$—S—$]_b$—$CH_3$ where a is 1-10 and b is 1-6. The term thioether also includes "dithioalkoxyalkyl" groups which refers to an alkyl group in which one or more —$CH_2$— groups are replaced with —S—S— (or two adjacent —$CH_2$— groups are each replaced with —S—). Unless otherwise specified preferred dithioalkoxyalkyl groups have from 3 to 30 carbon atoms and more preferably have 3 to 22 carbon atoms. Dithioalkoxylalkyl groups include groups of the formula: —$(CH_2)_a$—S—S—$(CH_2)_b$—$CH_3$, where a can be 1-15 and b is 0-25. Alkoxyalkyl, thioalkoxyalkyl and dithioalkoxyalkyl groups can be branched by substitution of one or more carbons of the group with alkyl groups.

The term "alkoxyalkylene" refers to a diradical of a branched or unbranched saturated hydrocarbon chain in which one or more —$CH_2$— groups are replaced with —O—, which unless otherwise indicated can have 1 to 10 carbon atoms, or 1-6 carbon atoms, or 2-4 carbon atoms. This term is exemplified by groups such as —$CH_2OCH_2$—, —$CH_2CH_2OCH_2CH_2$—, —$CH_2CH_2OCH_2CH_2OCH_2CH_2$— and more generally —$[(CR''_2)_a$—O—$]_b$—$(CR''_2)_c$—, where R'' is hydrogen or alkyl, a is 1-10, b is 1-6 and c is 1-10 or more preferably a and c are 1-4 and b is 1-3. Alkoxyalkylene groups may be branched, e.g., by substitution with alkyl group substituents.

The term "thioalkoxyalkylene" refers to a diradical of a branched or unbranched saturated hydrocarbon chain in which one or more —$CH_2$— groups are replaced with —S—, which unless otherwise indicated can have 1 to 10 carbon atoms, or 1-6 carbon atoms, or 2-4 carbon atoms. This term is exemplified by groups such as —$CH_2SCH_2$—, —$CH_2CH_2SCH_2CH_2$—, —$CH_2CH_2SCH_2CH_2SCH_2CH_2$— and more generally —$[(CR''_2)_a$—S—$]_b$—$(CR''_2)_c$—, where R'' is hydrogen or alkyl, a is 1-10, b is 1-6 and c is 1-10 or more preferably a and c are 1-4 and b is 1-3. Thioalkoxyalkylene groups may be branched, e.g., by substitution with alkyl group substituents. The term "dithioalkoxyalkylene" refers to a diradical of a branched or unbranched saturated hydrocarbon chain in which one or more —$CH_2$— groups are replaced with —S—S—, which unless otherwise indicated can have 1 to 10 carbon atoms, or 1-6 carbon atoms, or 2-4 carbon atoms. This term is exemplified by groups such as —$CH_2S$—$SCH_2$—, —$CH_2CH_2S$—$SCH_2CH_2$—, —$CH_2CH_2CH_2$—S—S—$CH_2CH_2CH_2$— and more generally —$(CR''_2)_a$—S—S—$(CR''_2)_c$—, where R'' is hydrogen or alkyl, a is 1-15, and c is 1-15 or more preferably a and c are 1-6. Dithioalkoxyalkylene groups may be branched, e.g., by substitution with alkyl group substituents. Preferable dithioalkoxyalkylene groups have one —S—S— group.

The term "amino" refers to the group —$NH_2$ or to the group —NR'R' where each R' is independently selected from the group consisting of hydrogen, alkyl, cycloalkyl, alkenyl, cycloalkenyl, alkynyl, aryl, heteroaryl and heterocyclic all of which are optionally substituted provided that both R's are not hydrogen.

The terms "aminoalkyl", "aminoalkeny" and "aminoalkynyl" refer to alkyl, alkenyl and alkynyl groups, respectively, carrying one or more amino substituents. There terms also apply to alkyl, alkenyl and alkynyl groups, respectively, in which one or more. —$CH_3$, —$CH_2$—, —CH—. or —CH═ groups are replaced with —NR'R', —NR'—, —N—, or —N═, where R' is as defined above.

The term "aminoaryl" refers to an aryl group substituted with one or more amino substituents.

Alkyl, alkenyl, alkynyl and aryl groups are optionally substituted as discussed herein and may, dependent upon the size of the alkyl group, have preferably from 1-10 substituent groups. Substituted alkyl groups include those that carry 1 to 8 substituents, 1 to 5 substituents, 1 to 3 substituents, and 1 or 2 substituents. Aryl groups can be optionally substituted with alkyl, alkenyl or alkynyl groups and alkyl, alkenyl and alkynyl groups can be optionally substituted with aryl groups. It is well understood in the art that substitution of certain substituents on certain carbon atoms in alkyl, alkenyl, alkynyl and aryl groups is not possible because the resulting substituted species is unstable to decomposition or reaction or simply because there is no useful method for synthesis of the substituted species. Substitutions of groups in the compounds of this invention include only those substitutions that can be prepared by known methods or by ready adaptation of known methods and that will result in a substituted compound that has a practically useful lifetime.

"Haloalkyl" refers to alkyl, as defined herein, substituted by one or more halides (e.g., F—, Cl—, I—, Br—) as defined herein, which may be the same or different. A haloalkyl group may be perhalogenated in which all hydrogens are replaced with halides. A haloalkyl group may, for example, contain 1-10 halide substituents. Haloalkyl groups also include those containing 1-5 halides, those containing 1-3 halide and those containing 1 halide. Representative haloalkyl groups include, by way of example, trifluoromethyl, pentafluoroethyl, 3-fluorododecyl, 12,12,12-trifluorododecyl, 2-bromooctyl, fluorocyclohexyl, 3-bromo-6-chloroheptyl, and the like. Haloalkyl groups include fluoroalkyl groups and perfluoroalkyl groups. Similarly "haloalkenyl" and "haloalkynyl", respectively refer to alkenyl groups and alkynyl groups carrying one or more halide substituents. These groups may, for example contain 1-10 halide substituents. These groups also include those containing 1-5 halides, those containing 1-3 halides and those containing 1 halide. Representative haloalkenyl and haloalkynyl groups include, by way of example, trifluoroethylene, trichloroethylene, 3,3,3-trifluoro-1,2-propene, and trifluoropropyne (—C≡C—CF$_3$). Haloalkenyl and haloalkynyl groups include fluoroalkenyl and perfluoroalkenyl as well as fluoroalkynyl groups.

"Haloaryl" refers to aryl groups as defined herein, substituted by one or more halides (e.g., F—, Cl—, I—, Br—) as defined herein, which may be the same or different. A haloaryl group may be perhalogenated in which all hydrogens are replaced with halides. Any one or more of the hydrogens in an aryl group can be replaced with a halide. A phenyl ring can, for example, have up to five halogen substituents on the ring. Haloaryl groups include those which have 1-10 halides, those having 1-5 halides, those having 1-3 halides and those having 1 or 2 halides. Haloaryl groups include fluoroaryl groups and perfluoroaryl groups. Representative haloaryl groups include para-chlorophenyl, para-fluorophenyl, ortho, ortho-difluorophenyl, meta, para-dichlorophenyl, ortho, ortho, para-trifluorophenyl.

"Hydroxylalkyl", "hydroxylalkenyl" and "hydroxylalkynyl" refers to alkyl, alkenyl and alkynyl groups, respectively, substituted with one or more hydroxides (hydroxyl groups). These groups can contain 1-10 hydroxide substituents. These groups also include those containing 1-5 hydroxides, those containing 1-3 hydroxides and those containing 1 or 2 hydroxides. Representative "Hydroxylalkyl", "hydroxylalkenyl" and "hydroxylalkynyl" groups include among many others, 3-hydroxypropyl, 2,3-dihydroxypropyl, 2,4-dihydroxybutyl, 3,4-dihydroxy-3-methylbutyl, 4-hydroxoxy-2,3-butenyl, 2-hydroxy-4,5-pentenyl, and 5-hydroxy-2,3-pentynyl.

"Hydroxyaryl" refers to aryl groups as defined herein, substituted by one or more hydroxides, which may be the same or different. Any one or more of the hydrogens in an aryl group can be replaced with a hydroxide. A phenyl ring can, for example, have up to five hydroxide substituents on the ring. Hydroxyaryl groups include those which have 1-10 hydroxides, those having 1-5 hydroxides, those having 1-3 hydroxides and those having 1 or 2 hydroxides. Representative hydroxyaryl groups include para-hydroxyphenyl, ortho, ortho-dihydroxyphenyl, meta, para-dihydroxyphenyl, ortho, ortho, para-trihydroxyphenyl.

As to any of the above groups which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

The invention relates generally to compounds of formula FX1, above, where formula variables are defined above. The invention further relates to pharmaceutical compositions containing a therapeutic amount of one or more compounds of formula FX1 in combination with a pharmaceutically acceptable carrier or excipient. The invention relates to the use of one or more compounds of formula FX1 alone or in combination with one another for modulation of cell death and/or apoptosis in a target cell. The invention use of one or more compounds of formula FX1 alone or in combination with one or more chemotherapeutic agents other than a compound of formula FX1.

The invention relates to the use of one or more compounds of FX1 alone or in combination with one or more chemotherapeutic agents other than a compound of formula FX1 for inhibiting the growth and/or metathesis of cancer cells.

In specific embodiments, the invention provides phosphonate esters, including those where Y is a halogen, particularly chlorine, of formula FX1 where the A, B and C rings are optionally substituted phenyl rings. More specifically, the A, B and C rings are phenyl rings or phenyl rings carrying one or more hydroxyl groups, halogen atoms, small alkyl groups (having 1-6 carbon atoms, preferably 1-3 carbon atoms), or small alkoxide groups (having 1-6 carbon atoms, preferably 1-3 carbon atoms).

In specific embodiments, the invention provides phosphonate esters, including those where Y is a halogen, particularly chlorine, of formula FX1 where one or more of the A, B and C rings are pyridyl rings which optionally carry one or more hydroxyl groups, halogen atoms, small alkyl groups (having 1, 2 or 3 carbon atoms), or small alkoxide groups (having 1, 2 or 3 carbon atoms) on ring carbon atoms.

In specific embodiments, the invention provides phosphonate esters, including those where Y is a halogen, particularly chlorine, of formula FX1 where one or more of the A, B and C rings are pyrimidyl rings which optionally carry one or more hydroxyl groups, halogen atoms, small alkyl groups (having 1, 2 or 3 carbon atoms), or small alkoxide groups (having 1, 2 or 3 carbon atoms) on ring carbon atoms.

In specific embodiments, the invention provides phosphonate esters, including those where Y is a halogen, particularly chlorine, of formula FX1 where one or more of the A, B and C rings are pyridazyl rings which optionally carry one or more hydroxyl groups, halogen atoms, small alkyl groups (having 1, 2 or 3 carbon atoms), or small alkoxide groups (having 1, 2 or 3 carbon atoms) on ring carbon atoms.

In specific embodiments, the invention provides phosphonate esters, including those where Y is a halogen, particularly chlorine, of formula FX1 where one or more of the A, B and C rings are pyrazyl rings which optionally carry one or more hydroxyl groups, halogen atoms, small alkyl groups (having 1, 2 or 3 carbon atoms), or small alkoxide groups (having 1, 2 or 3 carbon atoms) on ring carbon atoms.

In specific embodiments, one or more of $X_A$, $X_B$ or $X_C$ are halogen atoms, hydroxide groups, small alkyl groups or small alkoxide groups.

In specific embodiments, one of $X_A$, $X_B$ or $X_C$ is a halogen atom, hydroxyl group, small alkyl group or small alkoxide group.

In specific embodiments, $X_A$, $X_B$ or $X_C$ represent one or more non-hydrogen substituents in the meta and/or para positions on the A, B or C rings.

In specific embodiments, each of $X_A$, $X_B$ and/or $X_C$ represent a single non-hydrogen substituent on a ring. More specifically, each of $X_A$, $X_B$ and/or $X_C$ represent a single halogen, hydroxide, small alkyl or small alkoxide substituent on a ring. In more specific embodiments, each of $X_A$, $X_B$ and/or $X_C$ represent a single substituent in the para ring position and in particular represent a single halogen, hydroxide, small alkyl or small alkoxide substituent in a meta position on the ring. In more specific embodiments, each of $X_A$, $X_B$ and/or $X_C$ represent a single substituent in the meta ring position and in particular represent a single halogen, hydroxide, small alkyl or small alkoxide substituent in a meta position on the ring.

In specific embodiments, n is 0.

In specific embodiments, phosphonate esters of this invention are those of formula FX1 where Y is $OR^1$, but exclude those in which one or two of $X_A$, $X_B$ and/or $X_C$ represent a single OH group in the para-position on the ring.

In specific embodiments, phosphonate esters of this invention where Y is $OR^1$ are those of formula FX1 where Y is $OR^1$, but exclude those in which one or two of $X_A$, $X_B$ and/or $X_C$ represent a single alkoxide group in the para-position on the ring.

In specific embodiments, phosphonate esters of this invention are those of formula FX1 where Y is $OR^1$, but exclude those in which one or two of $X_A$, $X_B$ and/or $X_C$ represent a single methoxide or ethoxide group in the para-position on the ring.

In specific embodiments, phosphonate esters of this invention are those of formula FX1 where Y is $OR^1$, but exclude phosphonate esters in which n is 0, $R^1$ and $R^2$ are both unsubstituted alkyl groups and one or two of $X_A$, $X_B$ and/or $X_C$ represent a single OH group in the para-position on the ring.

In specific embodiments, phosphonate esters of this invention are those of formula FX1, but exclude phosphonate esters in which n is 0, $R^1$ and $R^2$ are both unsubstituted alkyl groups and one or two of $X_A$, $X_B$ and/or $X_C$ represent a single alkoxide group in the para-position on the ring.

In specific embodiments, phosphonate esters of this invention are those of formula FX1, but exclude phosphonate esters in which n is 0, $R^1$ and $R^2$ are both unsubstituted alkyl groups and one or two of $X_A$, $X_B$ and/or $X_C$ represent a single methoxide or ethoxide group in the para-position on the ring.

In specific embodiments, phosphonate esters of this invention are those of formula FX1, but exclude phosphonate esters in which n is 0, $R^1$ and $R^2$ are both methyl, ethyl or propyl groups and one or two of $X_A$, $X_B$ and/or $X_C$ represent a single OH group in the para-position on the ring.

In specific embodiments, phosphonate esters of this invention are those of formula FX1, but exclude phosphonate esters in which n is 0, $R^1$ and $R^2$ are both methyl, ethyl or propyl groups and one or two of $X_A$, $X_B$ and/or $X_C$ represent a single alkoxide group in the para-position on the ring.

In specific embodiments, phosphonate esters of this invention are those of formula FX1, but exclude phosphonate esters in which n is 0, $R^1$ and $R^2$ are both methyl, ethyl or propyl groups and one or two of $X_A$, $X_B$ and/or $X_C$ represent a single methoxide or ethoxide in the para-position on the ring.

In specific embodiments, phosphonate esters of this invention are those of formula FX1, but exclude phosphonate esters in which n is 0, $R^1$ and $R^2$ are both unsubstituted alkyl groups and each of $X_A$, $X_B$ and/or $X_C$ are hydrogens.

In specific embodiments, $OR^2$ is not replaced with a halogen.

In specific embodiments, phosphonate esters of this invention are those of formula FX1, where $R^1$ and $R^2$ are groups other than ethyl or methyl groups.

In specific embodiments, phosphonate esters of this invention are those of formula FX1, where $R^1$ and $R^2$ are groups other than alkyl groups having 1-3 carbon atoms.

In specific embodiments, phosphonate esters of this invention are those of formula FX1, where n is 0, each of $X_A$, $X_B$ and/or $X_C$ are hydrogens and $R^1$ and $R^2$ are groups other than alkyl groups having 1-3 carbon atoms.

In specific embodiments, phosphonate esters of this invention are those of formula FX1, where n is 0, each of $X_A$, $X_B$ and/or $X_C$ are hydrogens and $R^1$ and $R^2$ are groups other than ethyl and methyl groups.

In specific embodiments, phosphonate esters of this invention are those of formula FX1, where $R^1$ and $R^2$ are groups other than unsubstituted phenyl groups.

In specific embodiments, phosphonate esters of this invention are those of formula FX1, where n is 0 and $R^1$ and $R^2$ are groups other than unsubstituted phenyl groups.

In specific embodiments, phosphonate esters of this invention are those of formula FX1, where n is 0, each of $X_A$, $X_B$ and/or $X_C$ are hydrogens, and $R^1$ and $R^2$ are groups other than unsubstituted phenyl groups.

Ring positions on the A, B and C rings of formula FX1 are defined as ortho, meta or para ring positions relative to the bond connecting the ring to the carbon atom as illustrated for ring A:

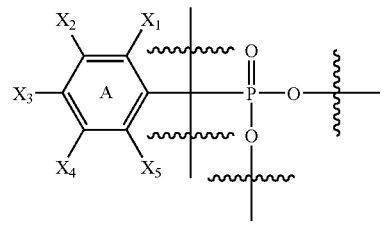

where substituents $X_1$ and $X_5$ are ortho substituents, substituents $X_2$ and $X_4$ are meta substituents and substituent $X_3$ is the para substituent. It will be appreciated that other naming conventions can be employed to designate the positions of substituents on a given ring.

In specific embodiments, wherein $X_A$, $X_B$, and/or $X_C$ represent non-hydrogen ring substituents, independently selected from the group consisting of alkyl, alkoxide, thiol, thioalkoxide, amine (—N(R')$_2$), R'—CO—, R'O—CO—, (R')$_2$N—CO—, R'O—COO—, (R')$_2$N—COO—, ether, thioether, alkenyl, alkynyl, wherein carbon atoms of the groups can be optionally substituted, $X_A$, $X_B$, $X_C$ groups contain 1-6 carbon atoms. In other specific embodiments, R' of such substituent groups are selected from hydrogen, methyl, ethyl, propyl, butyl, pentyl or hexyl groups which may be optionally substituted. In specific embodiments, $X_A$, $X_B$, and/or $X_C$ represent non-hydrogen ring substituents, selected from the group consisting of alkyl, alkoxide, R'—CO—, R'O—CO—, R'O—COO—, ether, alkenyl, and/or alkynyl groups where R' is hydrogen or optionally substituted alkyl groups. In specific embodiments, carbon atoms of one or more $X_A$, $X_B$, and/or $X_C$ substituents are substituted with one or more halogen atoms and/or one or more hydroxide groups.

In specific embodiments, $X_A$, $X_B$, and/or $X_C$ are selected from the group consisting of fluorine, chlorine, hydroxide, fluorinated alkyl, fluorinated alkoxy, fluorinated alkenyl, fluorinated alkynyl, chlorinated alkyl, chlorinated alkoxy, chlorinated alkenyl, and/or chlorinated alkynyl groups.

In specific embodiments, $X_A$, $X_B$, and/or $X_C$ are selected from the group consisting of alkyl groups, alkenyl groups and/or alkynyl groups and particularly those having 1-6 carbon atoms and particularly those in which the alkyl, alkenyl or alkynyl groups is substituted with one or more hydroxide groups.

In specific embodiments, $X_A$, $X_B$, and/or $X_C$ are selected from the group consisting of hydrogen, hydroxide and/or alkyl groups which are substituted with one or more hydroxide groups.

In specific embodiments, $X_A$, $X_B$, and/or $X_C$ groups contain from 1 to 6 carbon atoms. In other specific embodiments, $X_A$, $X_B$, and/or $X_C$ groups contain from 3 to 8 carbon atoms. In other specific embodiments, $X_A$, $X_B$, and/or $X_C$ groups contain from 8 to 12 carbon atoms. In yet other specific embodiments, $X_A$, $X_B$, and/or $X_C$ groups contain more than 10 carbon atoms.

In specific embodiments, $X_A$, $X_B$, and/or $X_C$ groups are selected from the group consisting of amine (—N(R")$_2$), R"CO—, R"O—CO—, (R")$_2$N—CO—, R"O—COO—, and (R")$_2$N—COO— where R", independently of one another, are alkyl groups optionally substituted with one or more halogens or hydroxides. In other specific embodiments, $X_A$, $X_B$, and/or $X_C$ groups are selected from the group consisting of amine (—N(R")$_2$), R"—CO—, R"O—CO—, (R")$_2$N—CO—, R"O—COO—, and (R")$_2$N—COO—where R", independently of one another, are aryl groups optionally substituted with one or more halogens or hydroxides.

In specific embodiments, $R^1$ and $R^2$, independently of one another, are selected from the group consisting of unsubstituted alkyl, alkenyl, alkynyl, ether, thioether, or aryl groups. In specific embodiments, $R^1$ and $R^2$, independently of one another are alkyl alkenyl, alkynyl, ether, thioether, or aryl groups. which are optionally substituted with one or more halogens, hydroxide, alkyl, or alkoxide groups.

In specific embodiments, $R^1$ and $R^2$ are the same groups. In other specific embodiments, $R^1$ and $R^2$ are different groups.

In specific embodiments, $R^1$ and $R^2$ are halogenated alkyl, alkenyl or alkynyl groups. In specific embodiments, $R^1$ and $R^2$ are fluorinated alkyl, alkenyl or alkynyl groups. In specific embodiments, $R^1$ and $R^2$ are fluorinated alkyl groups. In specific embodiments, $R^1$ and $R^2$ are fluorinated alkyl groups comprising a —CF$_3$ moiety.

In specific embodiments, at least one of $R^1$ or $R^2$ is [(—CH$_2$)$_m$-M-R$_3$]:

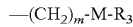

—(CH$_2$)$_m$-M-R$_3$

Where m is 0 or an integer ranging from 1 to 6 (preferably 1 or 2), M is a cyclic alkylene, cyclic alkenylene, heterocyclic alkylene, arylene or heteroarylene and R$_3$ is an optionally substituted alkyl, alkenyl, alkynyl or aryl group having from 2-20 carbon atoms. R$_3$ is optionally substituted with one or more non-hydrogen substituents selected from the group consisting of optionally substituted with one or more halogens, hydroxides, thiols, amine (—N(R")$_2$), R"O—CO—, (R")$_2$N—CO—, R"O—COO—, (R")$_2$N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments R$_3$ is a —(CH$_2$)$_r$COOR$_5$ group where r is an integer ranging from 1 to 20 (including 1-3, 1-6, 1-10, 8-20, among others) and R$_5$ is hydrogen or an optionally substituted alkyl, alkenyl, alkynyl or aryl group.

In specific embodiments, at least one of $R^1$ or $R^2$ is an alkyl group substituted with an R'O—CO—, (R')$_2$N—CO—, R'O—COO—, or (R')$_2$N—COO— where R' is defined above and is in particular an alkyl group. More specifically at least one of $R^1$ or $R^2$ is an alkyl group substituted with an R'O—CO— where R' is hydrogen or an alkyl group.

In specific embodiments, $R^1$ and $R^2$ are methyl, ethyl or propyl groups. In specific embodiments $R^1$ and $R^2$ are alkyl groups other than methyl groups. In specific embodiments $R^1$ and $R^2$ are alkyl groups other than ethyl groups.

In specific embodiments, $R^1$ and $R^2$ are alkyl groups having 3 to 6 carbon atoms which are optionally substituted with one or more halogens, particularly fluorines, or hydroxide groups. In specific embodiments, $R^1$ and $R^2$ are alkyl groups having 6-10 carbon atoms which are optionally substituted with one or more halogens, particularly fluorines, or hydroxide groups. In specific embodiments, $R^1$ and $R^2$ are alkyl groups having more than 10 carbon atoms which are optionally substituted with one or more halogens, particularly fluorines, or hydroxide groups. In specific embodiments, $R^1$ and $R^2$ are branched alkyl groups optionally substituted with one or more hydroxide groups.

In specific embodiments, $R^1$ and $R^2$ are alkenyl groups containing a single double bond which are optionally substituted with one or more halogens, particularly fluorine, or one or more hydroxide groups.

In specific embodiments, $R^1$ and $R^2$ are alkynyl groups containing a single triple bond which are optionally substituted with one or more halogens, particularly fluorine, or one or more hydroxide groups.

In specific embodiments, $R^1$ and $R^2$ together form an optionally substituted alkylene, or alkenylene diradical having 2 carbon atoms. In specific embodiments, $R^1$ and $R^2$ together form a alkylene, or alkenylene group having 2 carbon atoms which is substituted with one or two R'—OCO— groups wherein R' is hydrogen or an alkyl group, particularly an alkyl groups having from 1 to 6 carbon atoms.

In specific embodiments, n in formula FX1 is 0 and in other embodiments n is 1.

In specific embodiments, neither of $R^1$ or $R^2$ is or contains a nucleoside. In other specific embodiments, neither of $R^1$ or $R^2$ is or contains an amino acid or a peptide.

In specific embodiments, $R^1$ and $R^2$ are not both methyl groups. In specific embodiments, $R^1$ and $R^2$ are not both ethyl groups. In specific embodiments, when one or two of $X_A$, $X_B$ and/or $X_C$ is hydroxide, then both of $R^1$ and $R^2$ cannot be methyl. In other specific embodiments, when one or two of $X_A$, $X_B$ and/or $X_C$ is a para-hydroxide substituent, then both of both of $R^1$ and $R^2$ cannot be methyl. In specific embodiments, when one or two of $X_A$, $X_B$ and/or $X_C$ is/are hydroxide, then both of $R^1$ and $R^2$ cannot be ethyl. In other specific embodiments, when one or two of $X_A$, $X_B$ and/or $X_C$ is/are a para-hydroxide substituent, then both of both of $R^1$ and $R^2$ cannot be ethyl.

In specific embodiments, Y is chlorine.

In specific embodiments, the invention provides compounds of formula FX2:

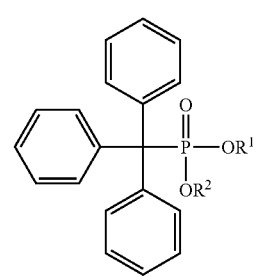

Formula FX2 where $R^1$ and $R^2$ are as defined above and in particular are alkyl, alkenyl or alkynyl groups having 1-3, 2-6, 4-10, 8-12, or greater than 10 carbon atoms. In specific embodiments, the invention provides compounds of formula FX2 where $R^1$ and $R^2$ are groups other than methyl, ethyl or propyl groups. In specific embodiments $R^1$ and $R^2$ are alkyl groups substituted with one or more halogens or one or more hydroxides.

In other specific embodiments, the invention provides compounds of formula FX2A:

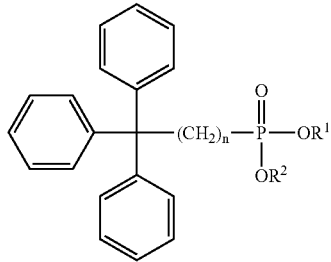

Formula FX2A wherein n is 1-6, preferably 1-2; and $R^1$ and $R^2$ are as defined above and in particular are alkyl, alkenyl or alkynyl groups having 1-3, 2-6, 4-10, 8-12, or greater than 10 carbon atoms. In specific embodiments $R^1$ and $R^2$ are alkyl groups substituted with one or more halogens or one or more hydroxides.

In other specific embodiments, the invention provides compounds of formula FX2B:

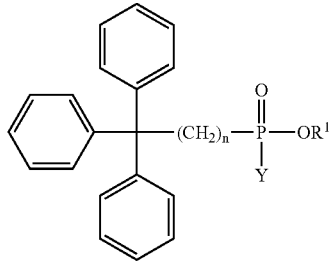

Formula FX2B wherein Y is a halogen, particularly Cl or F; n is 1-6, preferably 1-2; and $R^1$ is as defined above and in particular is an alkyl, alkenyl or alkynyl group having 1-3, 2-6, 4-10, 8-12, or greater than 10 carbon atoms. In specific embodiments R' is an alkyl group substituted with one or more halogens or one or more hydroxides.

In specific embodiments, the invention provides compounds of formula FX3:

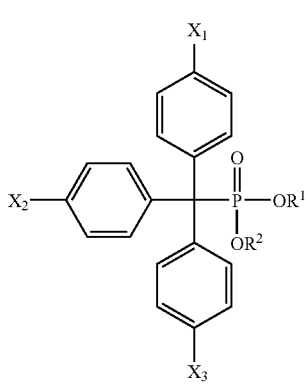

Formula FX3 where $X_{1-3}$ groups may be any of the groups listed above for $X_{A-C}$ and $R^1$ and $R^2$ are as defined above. In specific embodiments, any one or more of $X_{1-3}$ are halogens, particularly fluorines or are hydroxides and the remaining $X_{1-3}$ are hydrogens. In other embodiments, all of $X_{1-3}$ are halogens, particularly fluorines, or all of $X_{1-3}$ are hydroxides. In other specific embodiments, $R^1$ and $R^2$ are alkyl, alkenyl or alkynyl groups having 1-3, 2-6, 4-10, 8-12, or greater than 10 carbon atoms. In specific embodiments $R^1$ and $R^2$ are alkyl groups substituted with one or more halogens or one or more hydroxides.

In specific embodiments, the invention provides compounds of formula FX3, wherein $R^1$ and $R^2$ are groups other than alkyl groups. In specific embodiments, the invention provides compounds of formula FX3, wherein $R^1$ and $R^2$ are groups other than methyl ethyl or propyl groups. In specific embodiments, the invention provides compounds of formula FX3, wherein two or three of $X_1$, $X_2$ and $X_3$ are groups other than OH, or alkoxy groups. In specific embodiments, the invention provides compounds of formula FX3, wherein two or three of $X_1$, $X_2$ and $X_3$ are groups other than OH, methoxy or ethoxy groups. In specific embodiments, one or two of $X_{1-3}$ are OH groups and the others of $X_{1-3}$ are groups other than hydrogens. In specific embodiments, one or two of $X_{1-3}$ are OH groups and the others of $X_{1-3}$ are groups other than halogens. In specific embodiments, one or two of $X_{1-3}$ are OH groups and the others of $X_{1-3}$ are groups other than chlorines. In specific embodiments, the invention provides compounds of formula FX3 in which all of $X_{1-3}$ are OH groups or alkoxy groups. In specific embodiments, the invention provides compounds of formula FX3 in which all of $X_{1-3}$ are OH groups, methoxy groups or ethyoxy groups. In specific embodiments, the invention provides compounds of formula FX3 wherein one or two of $X_{1-3}$ are OH, methoxy or ethoxy groups and $R^1$ and $R^2$ are groups other than methyl, ethyl or propyl groups. In specific embodiments.

In specific embodiments, the invention provides compounds of formula FX3A:

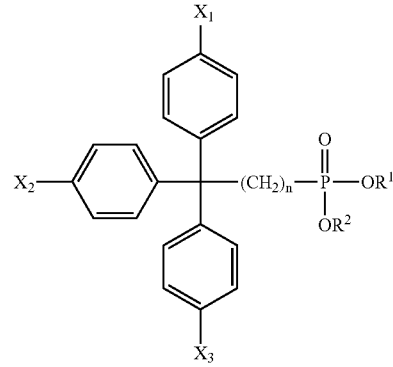

Formula FX3A where n is 1-6 or particularly 1 or 2; $X_{1-3}$ groups may be any of the groups listed above for $X_{A-C}$; and $R^1$ and $R^2$ are as defined above. In specific embodiments, any one or more of $X_{1-3}$ are halogens, particularly fluorines or are hydroxides and the remaining $X_{1-3}$ are hydrogens. In other embodiments, all of $X_{1-3}$ are halogens, particularly fluorines, or all of $X_{1-3}$ are hydroxides. In other specific embodiments, $R^1$ and $R^2$ are alkyl, alkenyl or alkynyl groups having 1-3, 2-6, 4-10, 8-12, or greater than 10 carbon atoms. In specific embodiments $R^1$ and $R^2$ are alkyl groups substituted with one or more halogens or one or more hydroxides.

In specific embodiments, the invention provides compounds of formula FX3B:

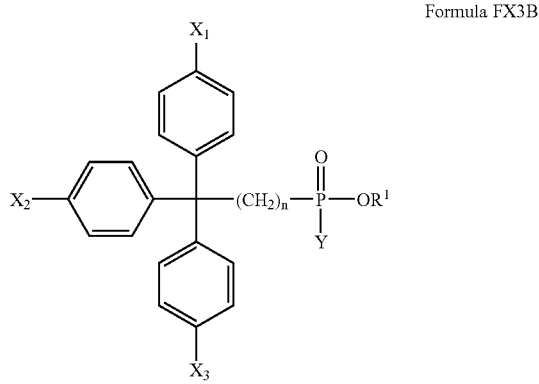

Formula FX3B where Y is a halogen, particularly chlorine or fluorine; n is 0, 1-6, or particularly 0 or 1 or 2; $X_{1-3}$ groups may be any of the groups listed above for $X_{A-C}$; and $R^1$ is as defined above. In specific embodiments, any one or more of $X_{1-3}$ are halogens, particularly fluorines or are hydroxides and the remaining $X_{1-3}$ are hydrogens. In other embodiments, all of $X_{1-3}$ are halogens, particularly fluorines, or all of $X_{1-3}$ are hydroxides. In other specific embodiments, $R^1$ is an alkyl, alkenyl or alkynyl group having 1-3, 2-6, 4-10, 8-12, or greater than 10 carbon atoms. In specific embodiments $R^1$ is an alkyl group substituted with one or more halogens or one or more hydroxides.

The invention further provides phosphonate esters of formula FX3D:

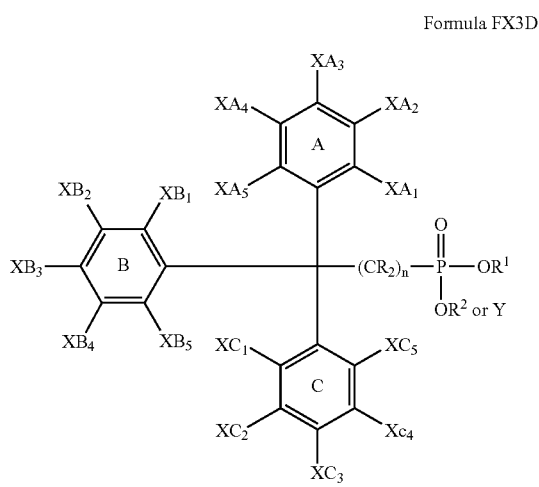

Formula FX3D where R, n, $R^1$, $R^2$, Y, Aryl rings A, B and C in general have the definitions as above or any combination of above definitions and wherein $XA_{1-5}$, $XB_{1-5}$, and $XC_{1-5}$ are substituents on the A, B and C rings respectively. Note that dependent upon the structure of the A, B or C ring, the ring may accommodate fewer than 5 substituents. In specific embodiments all of $XA_{1-5}$, $XB_{1-5}$, and $XC_{1-5}$ can be hydrogens, so that the rings are unsubstituted. The A, B and C rings may be substituted in the same way or differentially substituted. Each of $XA_{1-5}$, $XB_{1-5}$, and $XC_{1-5}$, may be the same substituent or different substituents. In general, each of $XA_{1-5}$, $XB_{1-5}$, and $XC_{1-5}$ can take any of the definitions listed above for $X_A$, $X_B$ or $X_C$ groups. Each ring may contain one, two, three, four or five non-hydrogen substituents dependent upon the structure of the ring and in particular dependent upon the number of carbons or heteroatoms in the ring which can carry a substituent. Preferred substituted A, B and C rings have one, two or three substituent. In a specific embodiment, substituted A, B or C rings carry a single para-substituent ($XA_3$, $XB_3$ or $XC_3$). In specific embodiments one, two or three of $XA_3$, $XB_3$ or $XC_3$ can be hydroxide groups or alkoxide groups. In specific embodiments one, two or three of $XA_3$, $XB_3$ or $XC_3$ can be hydroxide groups or alkoxide groups with other of $XA_{1-5}$, $XB_{1-5}$ and $XC_{1-5}$ groups being hydrogens. In specific embodiments, one, two or three of $XA_3$, $XB_3$ or $XC_3$ can be halogens. In specific embodiments one, two or three of $XA_3$, $XB_3$ or $XC_3$ can be halogens with other of $XA_{1-5}$, $XB_{1-5}$ and $XC_{1-5}$ groups being hydrogens.

In specific embodiments of formula FX3D, when n is 0 and two of $XA_3$, $XB_3$ or $XC_3$ are OH, the other of $XA_3$, $XB_3$ or $XC_3$ is a substituent other than a halogen or hydrocarbon group. In specific embodiments of formula FX3D, when n is 0 and two of $XA_3$, $XB_3$ or $XC_3$ are OH groups, then $R^1$ and $R^2$ are groups other than unsubstituted alkyl, arylalkyl or aryl groups and groups other than alkyl, arylalkyl or aryl groups substituted with halogens, or hydrocarbon groups. In specific embodiments of formula FX3D, when n is 0 all three of $XA_3$, $XB_3$ and $XC_3$ are OH groups. In specific embodiments of formula FX3D, when n is 0 and two of $XA_3$, $XB_3$ or $XC_3$ are OH, $OR^2$ is replaced with Y. In specific embodiments of formula FX3D, when n is 0 and two of $XA_3$, $XB_3$ or $XC_3$ are OH, then one or more of the A, B or C aryl rings contains one or more heteroatoms, particularly one or more N atoms. In specific embodiments of formula FX3D, when n is 0 and $XA_3$, and $XC_3$ are both OH, then neither of $XA_2$ or $XA_4$ is a halogen or methyl group. In specific embodiments of formula FX3D, when n is 0 and $XA_3$, and $XC_3$ are both OH, then neither of $XA_2$ or $XA_4$ is a halogen or a hydrocarbon group. In specific embodiments of formula FX3D, when n is 0 and $XA_3$, and $XC_3$ are both OH, then at least one of $XA_{1-2}$, $XA_{4-5}$, $XB_{1-5}$, $XC_{1-2}$, and $XC_{4-5}$ is a substituent other than a halogen, hydroxide or hydrocarbon group.

In specific embodiments, the invention provides compounds of formula FX4:

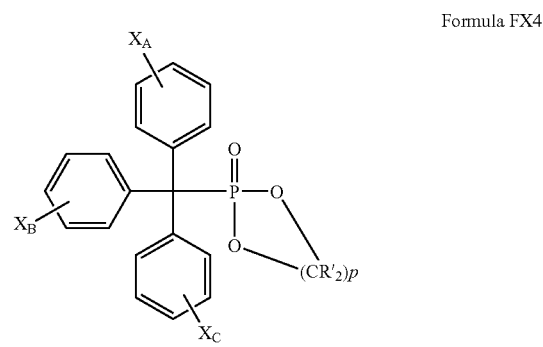

Formula FX4 where $X_{A-C}$ are as defined above, R', independent of other R' in the molecule, are hydrogen, or optionally substituted alkyl, alkenyl, alkynyl or aryl groups and p is an integer ranging from 2 to 6 and p is preferably 2, 3 or 4. R' are optionally substituted with groups selected from halogens, hydroxides, thiols, amine (—N(R")$_2$), R"O—CO—, (R")$_2$N—CO—, R"O—COO—, (R")$_2$N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments one or more R' is a R"O—CO— group where R" is hydrogen or an alkyl group.

In specific embodiments, the invention provides compounds of formula FX4A:

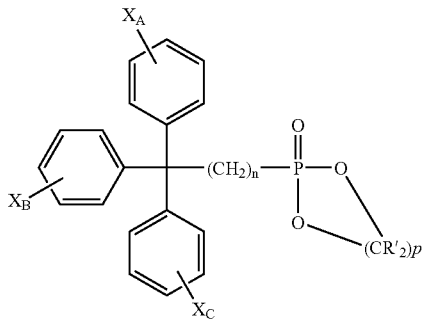

Formula FX4A where $X_{A-C}$ are as defined above, R', independent of other R' in the molecule, are hydrogen, or optionally substituted alkyl, alkenyl, alkynyl or aryl groups and p is an integer ranging from 2 to 6 and p is preferably 2, 3 or 4. R' are optionally substituted with groups selected from halogens, hydroxides, thiols, amine (—N(R")$_2$), R"O—CO—, (R")$_2$N—CO—, R"O—COO—, (R")$_2$N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments one or more R' is a R"O—CO— group where R" is hydrogen or an alkyl group.

In specific embodiments, the invention provides compounds of formula FX5:

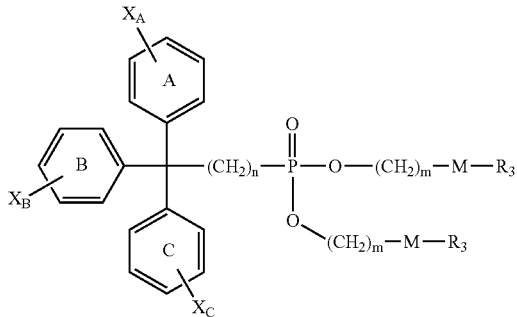

Formula FX5 where $X_{A-C}$ and n are as defined above and m is 0 or an integer ranging from 1 to 6 (preferably 1 or 2), M is an alkylene, alkenylene, cyclic alkylene, cyclic alkenylene, alkoxyalkyl, alkoxyalkylene, aminoalkyl, aminoalkylene, heterocyclic alkylene, arylene or heteroarylene and $R_3$ is an optionally substituted alkyl, alkenyl, alkynyl or aryl group having from 2-20 carbon atoms. $R_3$ is optionally substituted with one or more non-hydrogen substituents selected from the group consisting of optionally substituted with one or more halogens, hydroxides, thiols, amine (—N(R")$_2$), R"O—CO—, (R")$_2$N—CO—, R"O—COO—, (R")$_2$N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments $R_3$ is a —(CH$_2$)$_r$—COOR$_5$ group where r is an integer ranging from 1 to 20 (including 1-3, 1-6, 1-10, 8-20, among others) and $R_5$ is hydrogen or an optionally substituted alkyl, alkenyl, alkynyl or aryl groups.

In other specific embodiments, the invention provides compounds of formula FX5A:

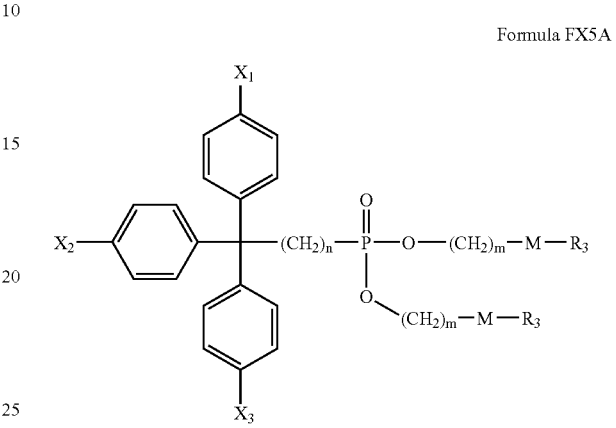

Formula FX5A where $X_{1-3}$ groups are those defined for $X_{A-C}$ and n, m, M and $R_3$ are as defined above in formula FX5.

In other specific embodiments, the invention provides compounds of formula FX5B:

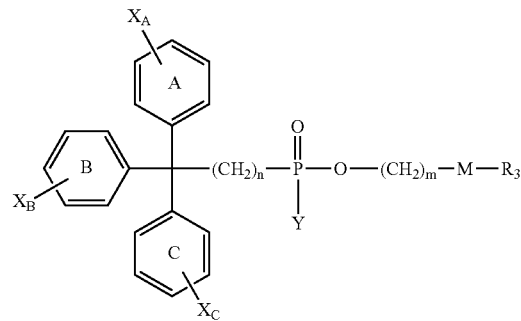

Formula FX5B where $X_{A-C}$ and n are as defined above, Y is a halogen, preferably chlorine or fluorine, m is 0 or an integer ranging from 1 to 6 (preferably 1 or 2), M is a cyclic alkylene, cyclic alkenylene, heterocyclic alkylene, arylene or heteroarylene and $R_3$ is an optionally substituted alkyl, alkenyl, alkynyl or aryl group having from 2-20 carbon atoms. $R_3$ is optionally substituted with one or more non-hydrogen substituents selected from the group consisting of optionally substituted with one or more halogens, hydroxides, thiols, amine (—N (R")$_2$), R"O—CO—, (R")$_2$N—CO—, R"O—COO—, (R")$_2$ N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments $R_3$ is a —(CH$_2$)$_r$—COOR$_5$ group where r is an integer ranging from 1 to 20 (including 1-3, 1-6, 1-10, 8-20, among others) and $R_5$ is hydrogen or an optionally substituted alkyl, alkenyl, alkynyl or aryl groups.

Non-limiting examples of the M diradical include among others:

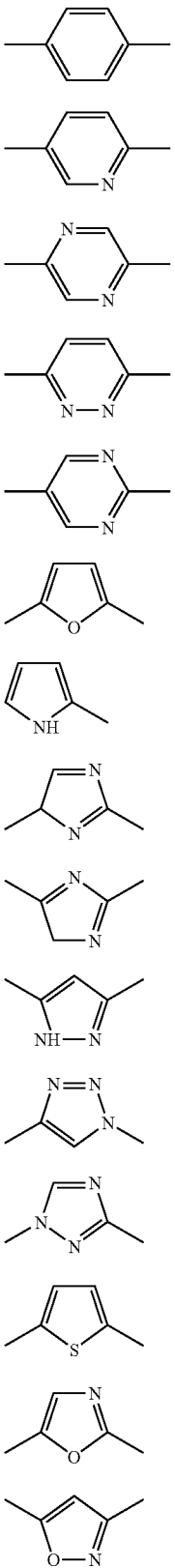

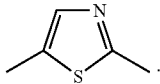

In specific embodiments, M is a heterocyclic alkylene or a heteroarylene having 5 or 6 ring atoms of which 1, 2 or 3 are nitrogen atoms. In more specific embodiments, M is a 1, 2, 3-triazolene diradical or a 1, 2, 4 triazolene diradical.

In specific embodiments, the invention provides compounds of formula FX5C:

Formula FX5C where $X_{A-C}$ and n are as defined above and m is an integer ranging from 1 to 6 (preferably 1 or 2) and $R_3$ is an optionally substituted alkyl, alkenyl, alkynyl or aryl group having from 1-20 carbon atoms. $R_3$ is optionally substituted with one or more non-hydrogen substituents selected from the group consisting of optionally substituted with one or more halogens, hydroxides, thiols, amine (—N(R")$_2$), R"O—CO—, (R")$_2$N—CO—, R"O—COO—, (R")$_2$N—COO—, nitro, cyano, and/or isocyano groups where R", independently of one another are alkyl, alkenyl, alkynyl or aryl groups optionally substituted with one or more halogens, hydroxides, thiols, nitro, cyano and/or isocyano groups. In specific embodiments $R_3$ is a —(CH$_2$)$_r$COOR$_5$ group where r is an integer ranging from 1 to 20 (including 1-3, 1-6, 1-10, 8-20, among others) and $R_5$ is hydrogen or an optionally substituted alkyl, alkenyl, alkynyl or aryl groups.

The invention further relates to pharmaceutical compositions containing a therapeutic amount of one or more compounds of any of formulas FX2, FX2A, FX2B, FX3, FX3A, FX3B, FX3C, FX3D, FX4, FX4A, FX5, FX5A, FX5B, or FX5C in combination with a pharmaceutically acceptable carrier or excipient. The invention relates to the use of one or more compounds of formulas FX2, FX2A, FX2B, FX3, FX3A, FX3B, FX3C, FX3D, FX4, FX4A, FX5, FX5A, FX5B, or FX5C alone or in combination with one another for modulation of cell death and/or apoptosis in a target cell. The invention use of one or more compounds of formulas FX2, FX2A, FX2B, FX3, FX3A, FX3B, FX3C, FX3D, FX4, FX4A, FX5, FX5A, FX5B, or FX5C alone or in combination with one or more chemotherapeutic agents other than a compound of formulas FX2, FX2A, FX2B, FX3, FX3A, FX3B, FX3C, FX3D, FX4, FX4A, FX5, FX5A, FX5B, or FX5C.

The invention relates to the use of one or more compounds of formulas FX2, FX2A, FX2B, FX3, FX3A, FX3B, FX3C, FX3D, FX4, FX4A, FX5, FX5A, FX5B, or FX5C alone or in combination with one or more chemotherapeutic agents other than a compound of formulas FX2, FX2A, FX2B, FX3, FX3A, FX3B, FX3C, FX3D, FX4, FX4A, FX5, FX5A, FX5B, or FX5C for inhibiting the growth and/or metathesis of cancer cells.

In specific embodiments, the invention provides compounds as illustrated in Scheme 1, including compounds CX1-CX17 as well as CX 20, CX40, RPhos2, and RPhos4, RPhos5, RPhos6, RPhos7, and RPhos8.

Compounds of the invention are useful generally for the treatment of any type of cancer. Certain compounds of the invention exhibit efficacy against a variety of different types of cancer cells. Compounds of the invention are useful general for the treatment of melanoma; leukemia, e.g., chronic myelogenous leukemia (CML), Acute lymphoblastic leukemia (ALL), and Acute Myelogenous Leukemia (AML); lymphoma; lung, renal, or brain cancer; CNS cancer; neuroblastoma; solid tumors and blood tumors.

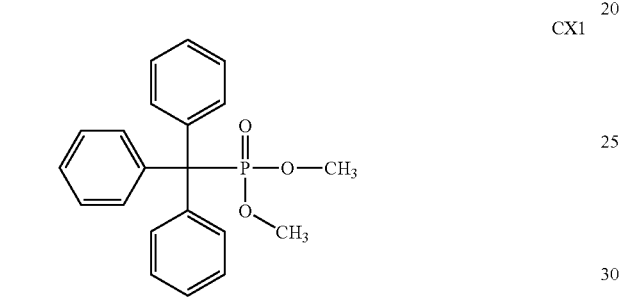

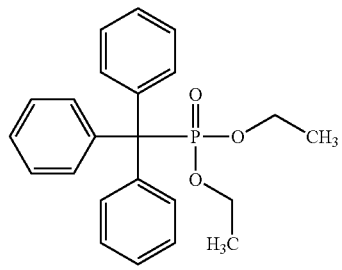

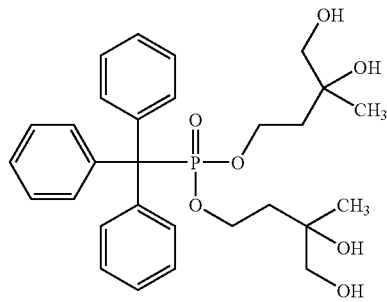

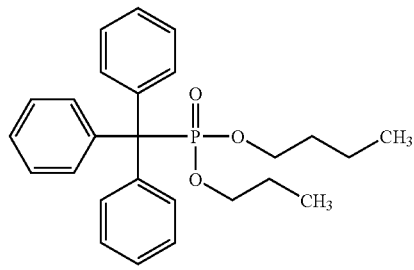

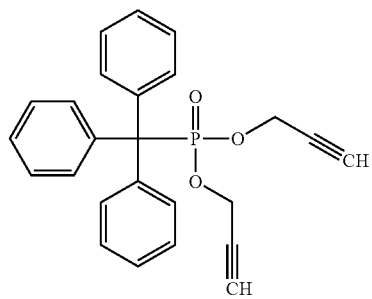

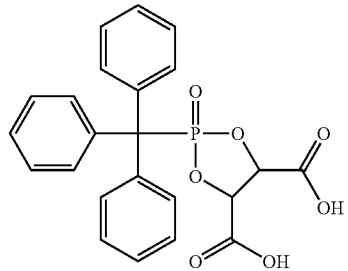

-continued
CX10
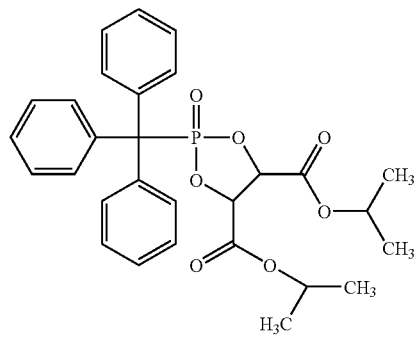
CX11
CX12
CX13
CX14
-continued
CX15
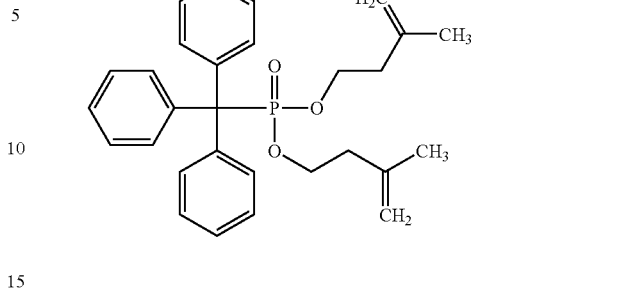
CX16
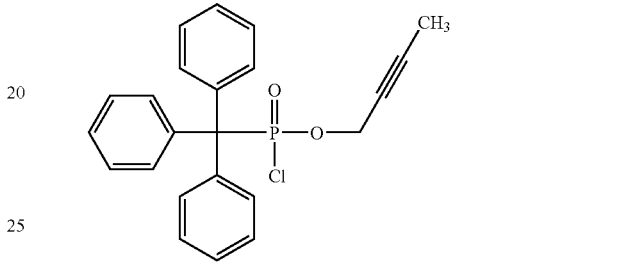
CX17
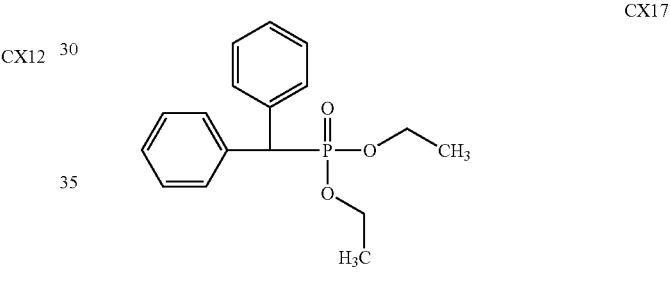
CX20
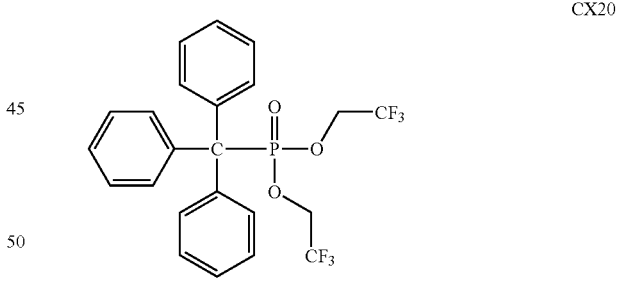
CX40
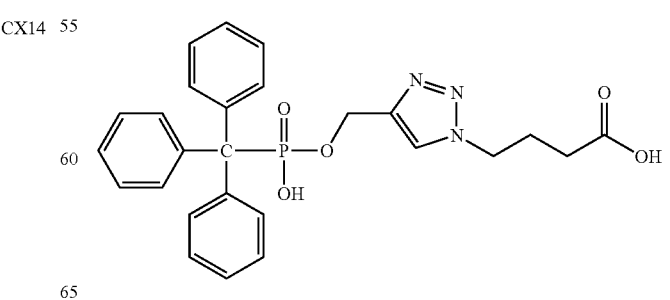

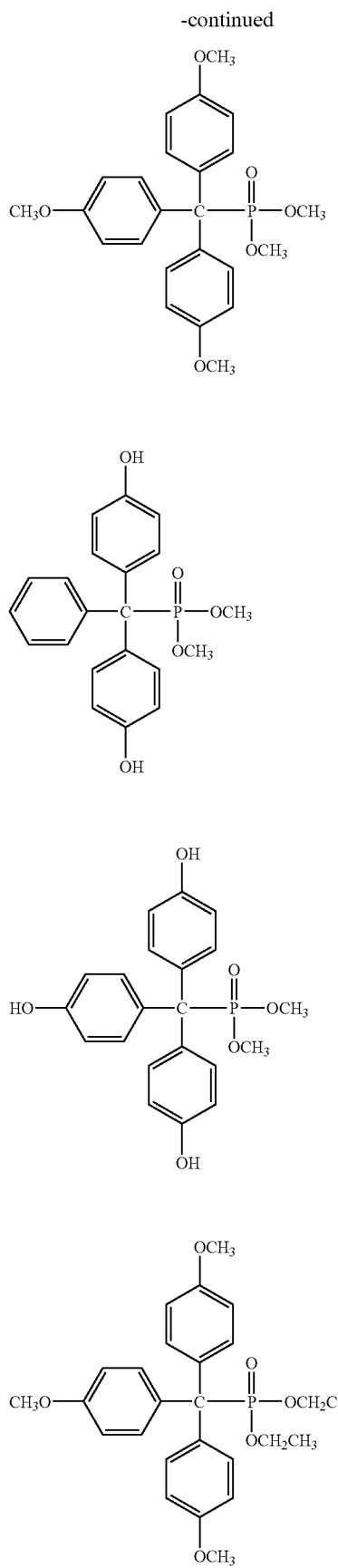

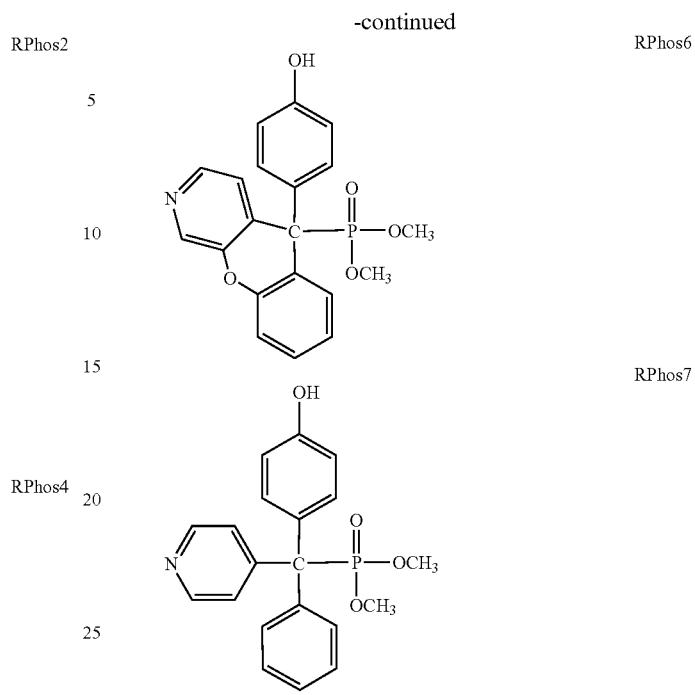

Compounds of the invention exhibit particular efficacy in melanoma cells. This is of particular interest because melanoma cells are generally known in the art to be resistant to chemotherapeutic agents. Melanoma is highly metastatic. The efficacy of compounds of the invention for inducing cell death in melanoma cells indicates usefulness of these compounds in the treatment of metastatic cancers, such as melanoma.

The following abbreviations are applicable herein: TPMP, triphenylmethylphosphonate esters; $IC_{50}$, inhibitory concentration at the 50% activity level.

The compounds of this invention can be synthesized employing methods as described herein in view of what is generally known in the art of chemical synthesis using reagents and starting materials that are commercially available or that can be prepared by known methods. Additionally methods can be employed as described in U.S. Pat. Nos. 3,847,866 and 3,702,879 (both by Bredereck, Iliopulos and Wieder) as well as in the following references:

Bhaftacharya A. K. and Thyagarajan, G. (1981) The Michaelis-Arbuzov Rearrangement, Chem. Rev. 81:415-430;

Haft, H. H. (1933) The Constitutions of Some Phosphorous Derivatives of Triphenylmethane, J. Chem. Soc., 776-786;

Iliopulos, M. I. and Wieder, H. Angew, Chemie (1965) 77: 618-619;

Lecouvey, M. (2005) Synlett., 3:425-428;

Shermolovich, Yu. G. et al. (1980) J. Gen. Chem. USSR (Engl. Translation) 50(4):649-652:

Tetradedron (1997) 53(37):12691-12698.

Boisselle, P. and Meinhardt N. A. (1962) J. Org. Chem. 27(5): 1828-1833; and

Anderson, G. W. (1956) J. Am. Chem. Soc. 78:2126-2131. Each of these references is incorporated by reference herein in its entirety to provide additional information for the synthesis of compounds of this invention. In particular several of these references provide details for the synthesis of phosphite starting materials useful in the Michaelis-Arbuzov reaction.

U.S. Pat. Nos. 3,702,879 and 3,847,866 relate to bis-(p-hydroxyphenyl) alkylphosphonic acid diesters which are reported to be useful for the preparation of condensation polymers. U.S. 3847866 and 3702879 may describe certain phosphonate ester compounds. Compounds of the invention are said to be those having the formula:

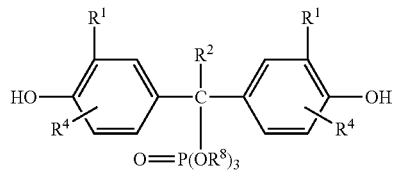

wherein $R^1$ represents an atom of hydrogen, or halogen, e.g. Cl, Br, F, or 1, or alkyl, $R^4$ represents an atom of hydrogen, or halogen, e.g. Cl, Br, F, or I, hydroxy, alkyl, cycloalkyl, arylalkyl, or aryl, which may or may not be substituted with substituents inert under the conditions of preparation, e.g. Cl, Br, F, I, or hydrocarbon substituents and $R^2$ and $R^3$ are alkyl, cycloalkyl, arylalkyl, aryl, which may or may not be substituted with substituents inert under the conditions of preparation, e.g. Cl, Br, F, or 1, or hydrocarbon substituents. Reportedly, when $R^1$, $R^2$, $R^3$, and/or $R^4$ are aliphatic, they may be straight- or branched-chain, and may be substituted or contain substituents such as halogen; the radicals $R^1$, $R^2$, $R^3$, and $R^4$ may be the same or different. The patent also purportedly relates to a method for making the diesters of the above formula in which a diester of formula:

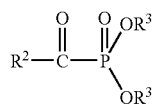

is reacted with a compound of formula:

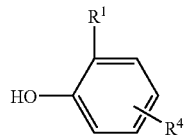

in the presence of a non-protonic Lewis-acid, such as AlCl3, $ZnCl_2$, $SnCl_4$, $TiCl_4$, $SO_3$, or a boron halide.

The invention further relates to pharmaceutical compositions containing a therapeutic amount of one or more of the compounds of Scheme 1 in combination with a pharmaceutically acceptable carrier, excipient or diluent The invention relates to the use of one or more of the compounds of Scheme 1 alone or in combination with one another for modulation of cell death and/or apoptosis in a target cell. The invention use of one or more of the compounds of Scheme 1 alone or in combination with one or more chemotherapeutic agents other than a compound of Scheme 1. The invention relates to the use of one or more of the compounds of Scheme 1 alone or in combination with one or more chemotherapeutic agents other than a compound of Scheme 1 for inhibiting the growth and/or metathesis of cancer cells.

Treatment methods of this invention comprise the step of administering a therapeutically effective amount of one or more compounds of this invention or a pharmaceutical composition containing one or more of such compounds to an patient in need of treatment. In specific embodiments, the compounds and compositions herein are useful for the treatment of cancer and the compounds and compositions are administered to a patient diagnosed with such cancers. As is understood in the art, the therapeutically effective amount of a given compound will depend at least in part upon, the mode of administration, any carrier or vehicle (e.g., solution, emulsion, etc.) employed, the specific disorder or condition, and the specific individual to whom the compound is to be administered (age, weight, condition, sex, etc.). The dosage requirements need to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined as is understood in the art.

The pharmaceutical composition of this invention can be in unit dosage form, e.g. as tablets or capsules. In such form, the composition is sub-divided in unit dose containing appropriate quantities of the active ingredient; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage employed to a given patient for a given disease or disorder can vary within wide limits and as is understood in the art will have to be adjusted to the individual requirements in each particular case.

Any suitable form of administration can be employed in the method herein.

The compounds of this invention can be administered in oral dosage forms including tablets, capsules, pills, powders, granules, elixirs, tinctures, suspensions, syrups and emulsions. Oral dosage forms may include sustained release or timed release formulations. The compounds of this invention may also be administered intravenously, intraperitoneally, subcutaneously, or intramuscularly, all using dosage forms well known to those of ordinary skill in the pharmaceutical arts.

Compounds of the invention can further be administered topically employing appropriate carriers. Such application may be particularly appropriate for the treatment of skin cancer, particularly melanoma.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol.

The compounds of this invention can also be administered to the eye, preferably as a topical opthalmic formulation. The compounds of this invention can also be combined with a preservative and an appropriate vehicle such as mineral oil or liquid lanolin to provide an opthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

It will be apparent to one of ordinary skill in the art that the compounds of this invention may be administered to a given patient for treatment of a given disease in more than one form, e.g., oral administration may be combined with intravenous administration or topically administration may be combined with oral or intravenous administration. In such cases, the dosage applied in one form may be adjusted in view of the dosage administered in another form.

The therapeutically active compounds of the invention can be administered alone, but generally will be administered with a pharmaceutical carrier, excipient or diluent selected upon the basis of the chosen route of administration and standard pharmaceutical practice. Pharmaceutical compositions and medicaments of this invention are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

The present invention provides methods of treating disorders, diseases conditions and symptoms in a patient which can be a mammal and particularly is a human, by administering to the individual in need of treatment or prophylaxis, a therapeutically effective amount of a compound of this invention. The result of treatment can be partially or completely alleviating, inhibiting, preventing, ameliorating and/or relieving the disorder, condition or one or more symptoms thereof. Administration includes any form of administration that is known in the art to be effective for a given type of disease or disorder, is intended to encompass administration in any appropriate dosage form and further is intended to encompass administration of a compound, pharmaceutically acceptable salt, solvate or ester thereof alone or in a pharmaceutically acceptable carrier thereof or administration of a prodrug derivative or analog of a compound of this invention which will form an equivalent amount of the active compound or substance within the body.

The invention expressly includes any pharmaceutically usable solvates of compounds according to the various formulas herein (e.g., FX1 etc.). The compounds of this invention can be solvated, e.g. hydrated. The solvation can occur in the course of the manufacturing process or can take place, e.g. as a consequence of hygroscopic properties of an initially anhydrous compound of the invention (hydration).

The compounds of this invention can be administered in any appropriate dosage forms and particularly in oral dosage forms including tablets, capsules, pills, powders, granules, elixirs, tinctures, suspensions, syrups and emulsions. Oral dosage forms may include sustained release or timed release formulations. The compounds of this invention may also be administered intravenously, intraperitoneally, subcutaneously, or intramuscularly, all using dosage forms well known to those of ordinary skill in the pharmaceutical arts.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water of appropriate purity, aqueous solutions (particularly containing additives as above, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

Compounds of the invention can have prodrug forms. Prodrugs of the compounds of the invention are useful in the methods of this invention. Any compound that can be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Compounds of the invention and compounds useful in the methods of this invention include those of the formulas described herein and pharmaceutically-acceptable salts and esters of those compounds. Salts include any salts derived from the acids of the formulas herein which are acceptable for use in human or veterinary applications. Pharmaceutically acceptable salts are used as known in the art and can comprise, for example, pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $Cl^-$, $Br^-$), sulfate, acetates (e.g., acetate, trifluoroacetate), ascorbates, aspartates, benzoates, citrates, and lactate. In an embodiment, the invention provides a therapeutic composition comprising one or more compounds and for each compound a pharmaceutically acceptable salt or ester thereof; wherein the compounds are present in the composition in an amount or in a combined amount effective for obtaining the desired therapeutic benefit. The therapeutic compositions of this invention optionally further comprise a pharmaceutically acceptable carrier as known in the art.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of members of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds, chemical groups or chemical moieties are intended to be exemplary, as it is known that one of ordinary skill in the art can name the same compounds, groups or moieties differently.

Many of the molecules disclosed herein contain one or more ionizable groups [i.e., groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

All references mentioned throughout this application, for example patent documents including issued or granted patents or equivalents; patent application publications; unpublished patent applications; and non-patent literature documents or other source material; are hereby incorporated by reference herein in their entireties, as though individually incorporated by reference. In the event of any inconsistency between cited references and the disclosure of the present application, the disclosure herein takes precedence. Some references provided herein are incorporated by reference to provide information, e.g., details concerning sources of starting materials, additional starting materials, additional reagents, additional methods of synthesis, additional methods of analysis, additional biological materials, additional cells, and additional uses of the invention.

References disclosing certain phosphonate compounds include:

Hornung, H.-D.; Klinkhammer, K.-W.; Schmidt, A. CH-π effect in dinuclear antimony (V) complexes with bridging phosphonato ligands. Main Group Metal Chemistry (1997), 20(3), 157-167;

Shi, Min; Okamoto, Yoshiki; Takamuku, Setsuo. Photolysis of diaryl triphenylmethylphosphonates. Bulletin of the Chemical Society of Japan (1990), 63(4), 1269-71;

Shi, Min; Okamoto, Yoshiki; Takamuku, Setsuo. Photolysis of (triarylmethyl)phosphonic acids and their esters. Bulletin of the Chemical Society of Japan (1990), 63(2), 453-60;

Min, Shi; Okamoto, Yoshiki; Takamuku, Setsuo. Photolysis of triphenylmethylphosphonic acid and its dimethyl esters: a novel photochemical generation of dimethoxyphosphinyl(phenyl)carbene by α,α-elimination of phenyl groups. Journal of the Chemical Society, Chemical Communications (1989), (3), 151-3;

Hatt, Harold H. Constitution of some phosphorus derivatives of triphenylmethane. Journal of the Chemical Society (1933), 776-86;

Johansson, Tommy; Stawinski, Jacek. Studies on the synthesis of picolylphosphonate diesters. Collection Symposium Series (2002), 5 (Chemistry of Nucleic Acid Components), 81-86;

Kondo, Akihiro; Obata, Takashi. Electrophotographic photoreceptor containing benzofuran-styryl compound and method of preparing ther compound. Published Japanese Patent application 2002-123013;

Zhou, Yeping; Wroblewski, Andrzej E.; Verkade, John G. Reactions of 4-alkyl-1-trityl-1-phospha-2,6,7-trioxabicyclo[2.2.2]octane cations with bases. Phosphorus, Sulfur and Silicon and the Related Elements (1998), 132 183-206;

Kers, Annika; Stawinski, Jacek; Dembkowski, Leszek; Kraszewski, Adam. Aryl H-phosphonates. 7. Studies on the formation of phosphorus-carbon bond in the reaction of trityl and benzyl halides with dialkyl and diphenyl H-phosphonates. Tetrahedron (1997), 53(37), 12691-12698;

Witt, Dariusz; Rachon, Janusz. Reactivity of the acids of trivalent phosphorus and their derivatives. Part VIII. Reactivity of the >P—O— nucleophiles toward arylmethyl bromide systems. Further evidence for the X-philic substitution/SET tandem mechanism. Phosphorus, Sulfur and Silicon and the Related Elements (1996), 117 149-165;

Shi, Min; Okamoto, Yoshiki; Takamuku, Setsuo. Photolysis of (triarylmethyl)phosphonic acids and their esters. Bulletin of the Chemical Society of Japan (1990), 63(2), 453-60;

Gramstad, Thor; Tjessem, Kjell. Studies of hydrogen bonding. Part XXVIII. Hydrogen bond association of phenol with 5,5-dimethyl-2-oxo-1,3,2-dioxaphosphorinanes and diethylphosphonates. Acta Chemica Scandinavica, Series B: Organic Chemistry and Biochemistry (1977), B31(5), 345-53;

Malatesta, P. Phosphoric acid esters with high anticholinesterase activity. II. Paroxon analogs. Farmaco, Edizione Scientifica (1963), 18(10), 714-20;

Arbuzov, A. E.; Chang, Ching-Ling. Reaction of some substituted triarylhalomethanes with salts of dialkyl phosphonates. III. Reaction of crystalline triphenylchloromethane with sodium diethyl phosphonate. Izvestiya Akademii Nauk SSSR, Seriya Khimicheskaya (1963), (11), 1945-6;

Arbuzov, A. E.; Chang, Ching-Ling. Reaction of some substituted triarylchloro- and -bromo-methanes with salts of dialkyl phosphonates. Doklady Akademii Nauk SSSR (1962), 144 1039-41;

Arbuzov, A. E.; Abramov, V. S. Action of halo-substituted ethers on salts of dialkyl phosphites. Izvestiya Akademii Nauk SSSR, Seriya Khimicheskaya (1959), 3540; and Kopel'tsiv, Yu. A.; Kolesnikov, V. T.; Shermolovich, Yu. G.; Trotsenko, S. I.; Klep, V. Z. Phosphorylation of methylene-quinones. IV. Reaction of fuchsone and naphthofuchsone with di- and trialkyl phosphites. Zhurnal Obshchei Khimii (1986), 56(3), 588-92;

Shermolovich, Yu. G.; Markovskii, L. N.; Kopel'tsiv, Yu. A.; Kolesnikov, V. T. Reaction of fuchsone with di- and trialkylphosphites. Zhurnal Obshchei Khimii (1980), 50(4), 811-15. Each of these references is incorporated in its entirety herein for its disclosure of phosphonate compounds and synthesis thereof. Any one or more of the phosphonate compounds disclosed in any one of the references listed can be excluded from any of the claims herein.

All patents and publications mentioned herein are indicative of the levels of skill of those skilled in the art to which the invention pertains. References cited herein can indicate the state of the art as of their publication or filing date, and it is intended that this information can be employed herein, if needed, to exclude specific embodiments that are in the prior art. For example, when composition of matter are claimed herein, it should be understood that compounds known and available in the art prior to Applicant's invention, including compounds for which an enabling disclosure is provided in the references cited herein, are not intended to be included in the composition of matter claims herein.

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Thus as used herein, comprising is synonymous with including, containing, having, or characterized by, and is inclusive or open-ended. As used herein, "consisting of" excludes any element, step, or ingredient, etc. not specified in the claim description. As used herein, "consisting essentially of" does not exclude materials or steps that do not materially affect the basic and novel characteristics of the claim (e.g., relating to the active ingredient). In each instance herein any of the terms "comprising", "consisting essentially of" and "consisting of" may be replaced with either of the other two terms, thereby disclosing separate embodiments and/or scope which is not necessarily coextensive. The invention illustratively described herein suitably may be practiced in the absence of any element or elements or limitation or limitations not specifically disclosed herein.

Whenever a range is disclosed herein, e.g., a temperature range, time range, composition or concentration range, or other value range, etc., all intermediate ranges and subranges as well as all individual values included in the ranges given are intended to be included in the disclosure. This invention is not to be limited by the embodiments disclosed, including any shown in the drawings or exemplified in the specification, which are given by way of example or illustration and not of limitation. It will be understood that any subranges or individual values in a range or subrange that are included in the description herein can be excluded from the claims herein.

The invention may be further understood by the following non-limiting examples.

THE EXAMPLES

Example 1

Synthesis of Compounds

Compounds of this invention can be prepared by the Michaelis-Arbuzov reaction involving the reaction of trityl chloride or bromide and a trialkyl phosphite. See Scheme 2:

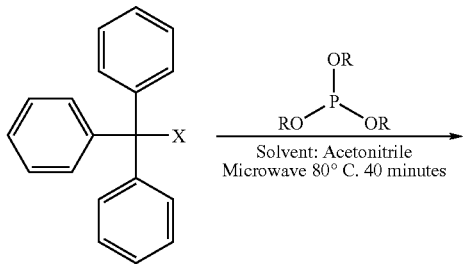

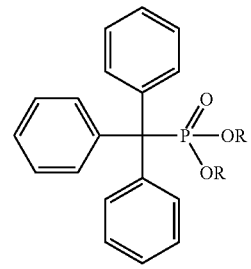

X = Cl, Br

See also, e.g., Chem. Rev. 1981, 81, 415-430; Tetrahedron., Vol. 53, No. 37, 12691-12698, 1997; Hatt; J. Chem. Soc.; 1933; 776; and Shermolovich, Yu. G.; Markovskii, L. N.; Kopel'tsiv, Yu. A.; Kolesnikov, V. T.; J. Gen. Chem. USSR (Engl. Transl.); 50; 4; 1980; 649-652.

The Michaelis-Arbuzov reaction can be employed using various substituted trityl halides and with selection of appropriate starting phosphites to prepare compounds of this invention.

Para-hydroxy derivatives, as exemplified by the derivative shown below can be synthesized by the following Scheme 3:

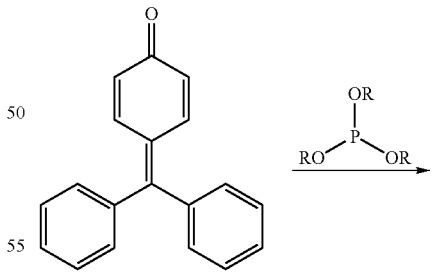

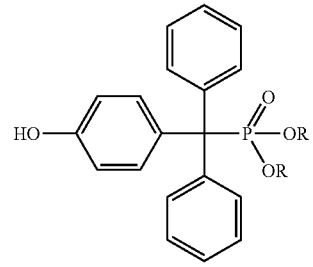

See Shermolovich, Yu. G.; Markovskii, L. N.; Kopel'tsiv, Yu. A.; Kolesnikov, V. T.; JGCHA4; J. Gen. Chem. USSR (Engl. Transl.); EN; 50; 4; 1980; 649-652; ZOKHA4; Zh. Obshch. Khim.; RU; 50; 4; 1980; 811-815.

Compound RPhos6 is synthesized as illustrated in Scheme 4:

Scheme 4:

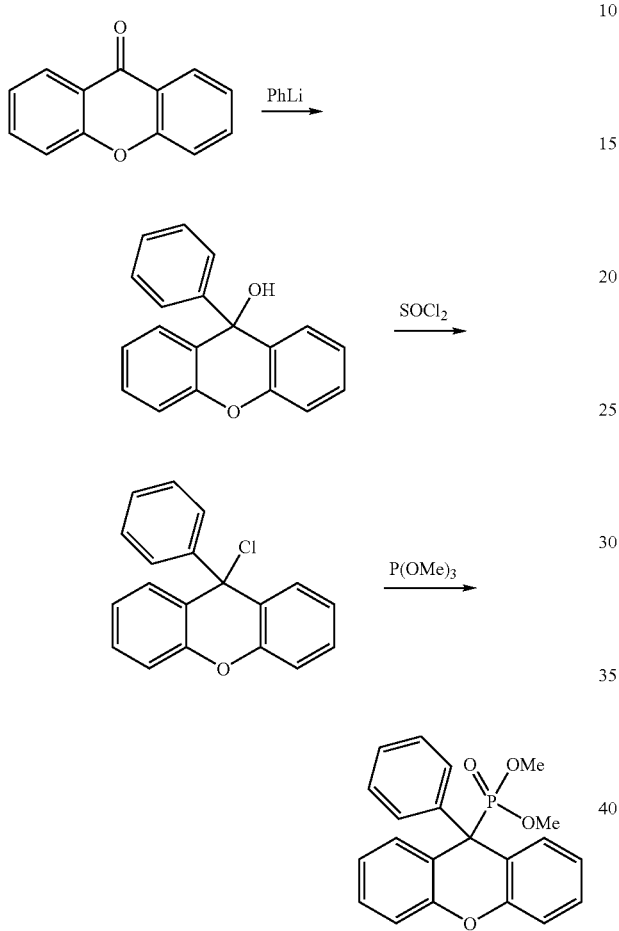

Analogs of compound RPhos6 wherein the moiety linking the two phenyl rings is —CR'''$_2$—, —CH$_2$—, —NH—, or —S— can be prepared by an analogous method with appropriate choice of starting material.

Compounds CX8 and CX14 are prepared as illustrated in Scheme 5.

Scheme 5:

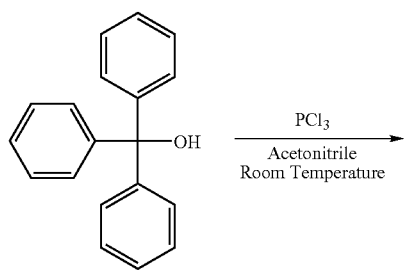

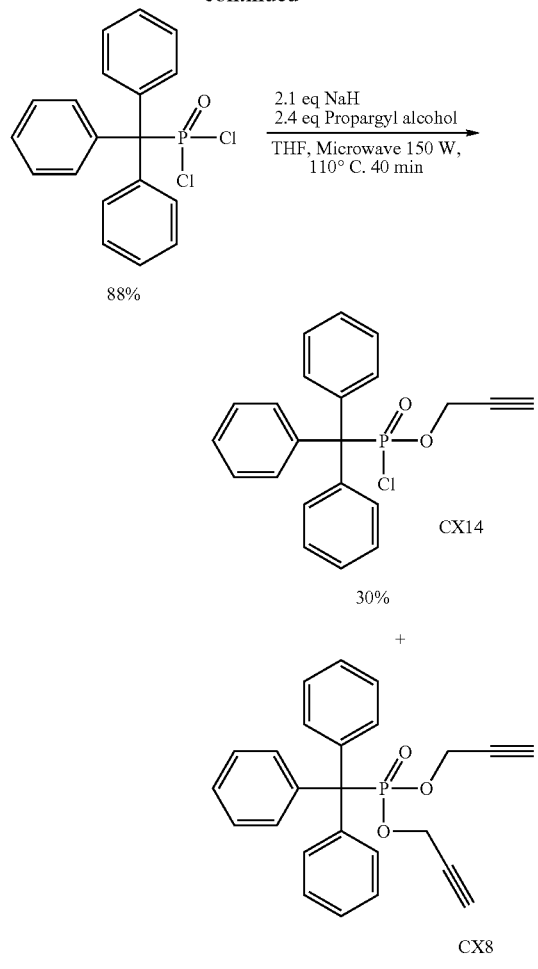

Compounds CX8 and CX14 are separated and purified employing techniques that are well-known in the art.

Di-hydroxy derivatives (as exemplified below) can be synthesized as illustrated in Iliopulos and Wieder; Angew. Chem.; 77; 1965; 618.

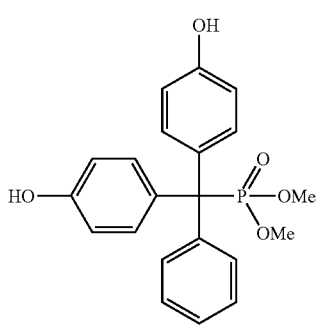

Figure 2:
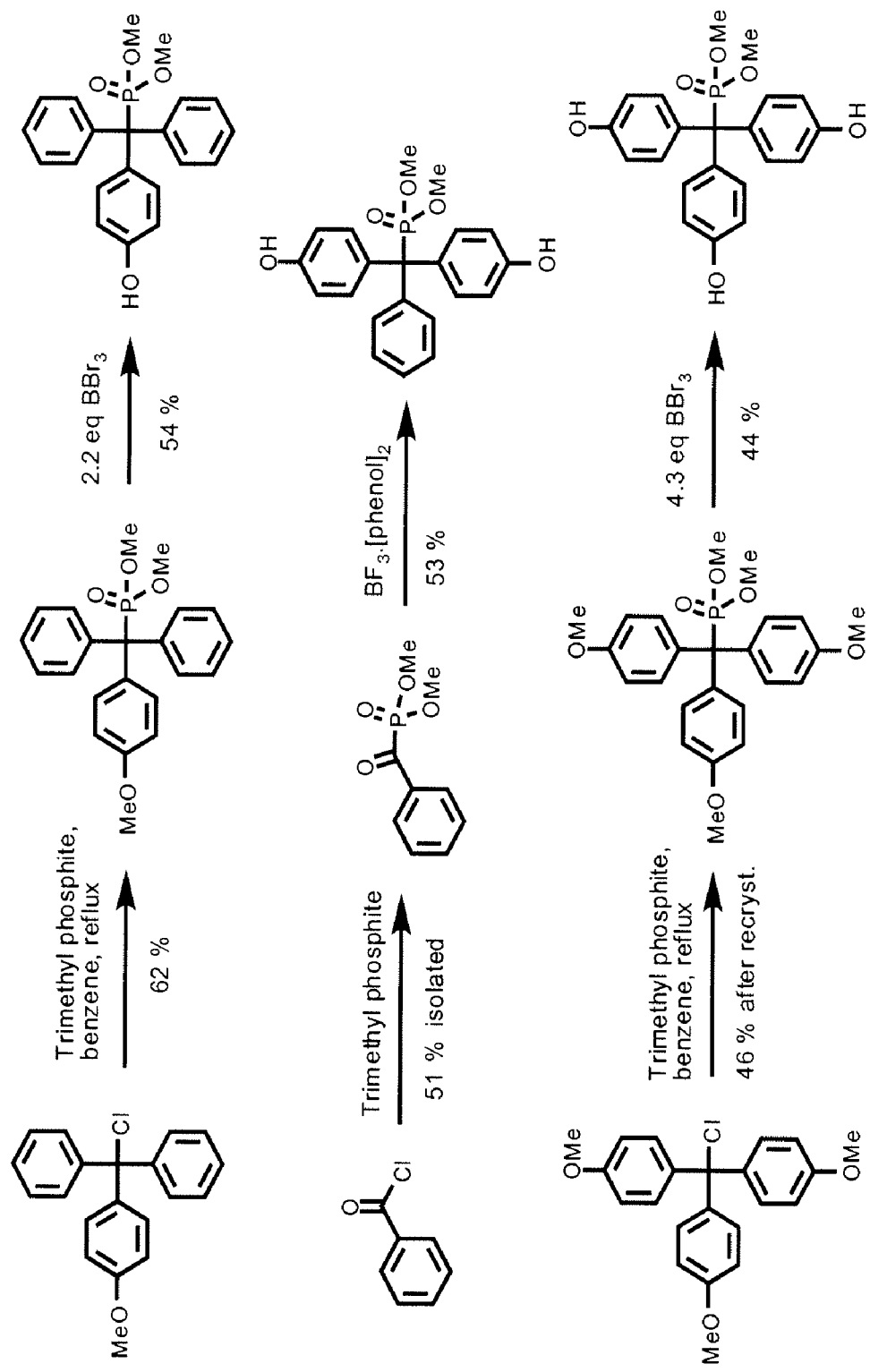
FIG. 2 illustrates methods of synthesis for compounds, including schemes for synthesis of various hydroxy derivatives.
Figure 3:
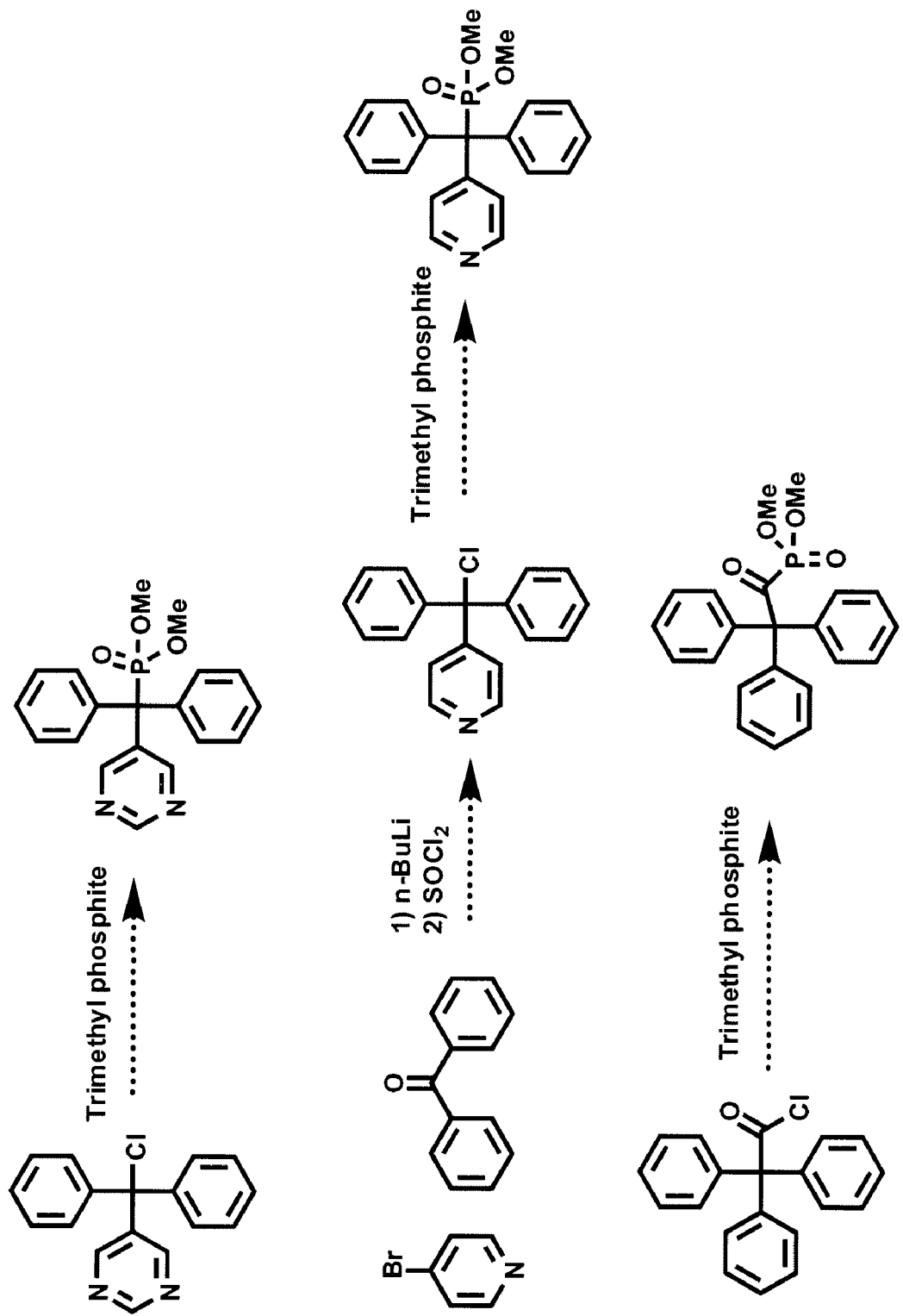
FIG. 3 illustrates methods of synthesis including schemes for further TPMP derivatives.
Figure 4:
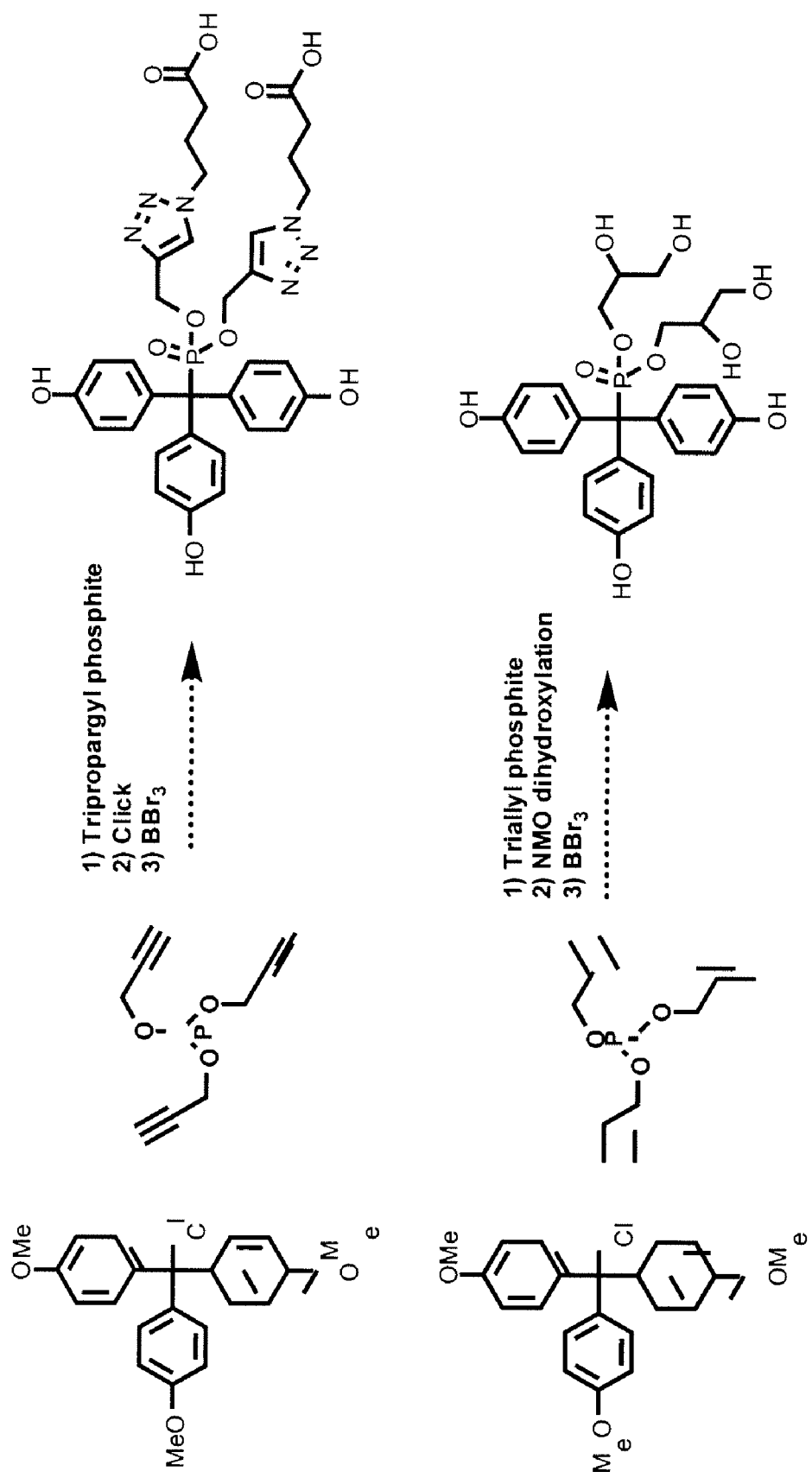
FIG. 4 illustrates additional methods of synthesis including schemes for further para-trihydroxy TPMP derivatives.

Specific examples as shown in FIGS. 1-4 can be used to prepare starting materials including phosphites and compounds. Phosphites useful as starting materials for synthesis of compounds of the invention are commercially available or can be prepared by methods well known in the art, particularly in view of the specific examples provided in FIGS. 1-4.

Example 2

Screening for Activity, Apoptotic Properties, and Toxicity

A single or multi-tiered system can be used to identify compounds that selectively induce apoptosis in cancer cells. First, all compounds can be screened at a selected concentration, e.g., 100 μM, in a high-throughput manner for their ability to induce death in one or more cancer cell lines such as HL-60 (leukemia) and U-937 (lymphoma). Those molecules exhibiting cytotoxicity in one or more cell lines are then evaluated for their apoptotic versus necrotic properties. Those compounds that induce apoptosis can then have their toxicity to non-cancerous cells, e.g., white blood cells, assessed. Potent compounds can be re-synthesized, purified, and tested at multiple concentrations to determine $IC_{50}$ values in the context of one or more cell lines, cells, or tissues.

Further experiments can assess whether the observed death from test compounds is due to apoptosis or necrosis. Cells exposed to the test compound are examined for one or several hallmarks of apoptotic cell death including strong induction of caspase-3 activity, staining with the apoptotic-specific dye JC-9 as assessed by flow cytometry, or other aspects. It is understood that JC-9 provides a sensitive readout on mitochondrial depolarization, and dyes of this class are commonly used to quantitate apoptosis (Cossarizza, A.; Salvioli, S. Methods Cell Biol. 2001, 63, 467-486). Evidence of apoptosis can be provided by microscopy, for example by detecting membrane blebbing and cell shrinkage.

The selectivity of a test compound for cancerous white blood cells over non-cancerous white blood cells is determined. For this experiment, the spleen from a euthanized mouse is harvested, and the splenocytes isolated. Mouse splenocytes are commonly used to assess the toxicity of small molecules. For examples see: (a) Prater, M. R.; Gogal, R. M.; Blaylock, B. L.; Longstreth, J.; Holladay, S. D. Food Chem. Toxicol. 2002, 40, 1863-1873. (b) Blake, C. A.; Nair-Menon, J. U.; Campbell, G. T. Endocrine 1997, 6, 243-249. (c) Yamaura, K.; Ogawa, K.; Yonekawa, T.; Nakamura, T.; Yano, S.; Ueno, K. Biol. Pharm. Bull. 2002, 25, 201-205. (d) Li, Q.; Hirata, Y.; Piao, S.; Minami, M. Toxicology 2000, 150, 179-189. The T-cells are then stimulated to grow by the addition of concanavalin A. For example, T-cells are purified from a heterogeneous splenocyte mixture, stimulated to grow with concanavalin A, and assessed for death after 72 h in the presence or absence of a selected concentration of the test compound (e.g., 100 to 500 μM). Thus we are able to identify small molecules that selectively induce apoptosis in cancerous white blood cells but are non-toxic toward non-cancerous white blood cells.

Example 3

Biological Assays

General Cell Culture Conditions: U-937 and HL-60 cell lines are grown in RPMI 1640 supplemented with 10% FBS and incubated at 37° C. in a 5% $CO_2$, 95% air atmosphere and are split as necessary, e.g., every two to three days. According to the American Type Culture Collection (ATCC), U-937 is a human cell line of histiocytic lymphoma tissue with monocyte morphology. See Sundstrom C, Nilsson K, Int. J. Cancer 17: 565-577, 1976. Also according to ATCC, HL-60 is a human cell line of a tissue type described as peripheral blood, promyeloblast, and acute promyelocytic leukemia, with myeloblastic morphology. See Gallagher R, et al., Blood 54: 713-733, 1979.

High-throughput Cell Death Assay I on Test Compounds: U-937 and HL-60 cells from cell culture are harvested by centrifugation at 250×g for 5 min. Cells are then resuspended in RPMI 1640+10% FBS, counted using a hemocytometer and diluted so that 20,000 cells are seeded into each well of a Corning 96-well flat bottom microtiter plate (Fisher, Chicago Ill.). Media is then added to bring the total volume of each well to 100 μL. Test compounds are transferred into the wells using a 96-pin transfer apparatus (V & P Scientific, San Diego Calif.) that transfers 0.2 μL of compound. The compounds are made up as 50 mM stock solutions in 100% EtOH, so one transfer gives a final concentration of 100 microM. Controls are performed in which only EtOH (containing no compound) is pin-transferred into wells containing cells. The cells are incubated with the compounds for 24 hours, and then cell death is quantitated. This quantitation is performed by addition of 20 microL of the MTS/PMS CellTiter 96 Cell Proliferation Assay reagent (Promega, Madison Wis.) to each well; this reagent is 3-(4,5-dimethylthiazol-2-yl)-5-(3-carboxymethoxyphenyl)-2-(4-sulfophenyl)-2H-tetrazolium, inner salt (MTS), and an electron coupling reagent, phenazine methosulfate (PMS). See Promega Technical Bulletin TB169, April, 2005.

The plates are incubated at 37° C. for approximately one hour until the colored product formed and the absorbance was then measured at 490 nm in a Spectra Max Plus 384 plate reader (Molecular Devices, Sunnyvale Calif.).

Determination of IC50 Values for test compounds. U-937 and HL-60 cells from cell culture are harvested by centrifugation at 250×g for 5 min. Cells are then resuspended in RPMI 1640+10% FBS, counted using a hemocytometer and diluted so that 10,000 cells are seeded in to each well of a Corning 96-well flat bottom microtiter plate (Fisher, Chicago Ill.). Media is then added to bring the total volume of each well to 100 μL. Each compound is weighed and then diluted with EtOH to make a 100 mM stock solution. The compounds are added at 9 or more different concentration in 1 μL of EtOH. After a 72 h incubation (37° C. in a 5% $CO_2$, 95% air atmosphere) cell death is quantitated by addition of 20 μL of the MTS/PMS CellTiter 96 Cell Proliferation Assay reagent (Promega, Madison Wis.) to each well. The plates are incubated at 37° C. for approximately 1 hour until the colored product is formed and the absorbance is then measured at 490 nm in a Spectra Max Plus 384 plate reader (Molecular Devices, Sunnyvale Calif.). The $IC_{50}$ is taken as the concentration that caused 50% cell death.

Caspase-3 Activity Assay: The amount of caspase-3 like protease activity can be determined by the amount of Ac-DEVD-pNA (N-acetyl-Asp-Glu-Val-Asp p-nitroanilide) cleaved per minute by cell lysates. To accomplish this, 100 microM of test compound is added to cell culture flasks containing 50 mL of 10×10⁶ U-937 cells/mL at 72, 48, 36, 24, 12 and 0 hours before harvesting. Cells are harvested by centrifugation, then counted and diluted with RPMI 1640 media to a concentration of 4×10⁶ cells/mL. 100 μL of the diluted cells are added to the wells of a 96-well plate in quadruplicate. The plate is then spun at 1000×g for 5 minutes to pellet the cells. The cells are washed with 100 μL of PBS (137 mM NaCl, 2.7 mM KCl, 4.3 mM $Na_2HPO_4$, 1.4 mM $KH_2PO_4$, pH 7.4) and resuspended in 150 μL of ice cold Caspase Assay Buffer (50 mM HEPES, 100 mM NaCl, 10 mM DTT, 0.1 mM EDTA, 0.1% CHAPS and 10% Glycerol, pH 7.4). Each well is then sonicated to lyse the cells. 90 μL of cell lysate is transferred from each well into a new plate. Caspase Assay Buffer is added to wells as a control. Ac-DEVD-pNA (Sigma, St. Louis Mo.) is added into each well to give a final concentration of 200 μM. The plate is then read every 2 minutes at 405 nm for 2 hours in a Spectra Max Plus 384 plate reader (Molecular Devices, Sunnyvale Calif.). The slope of the linear portion for each compound is then determined and any cleavage of the substrate in the control wells is subtracted out. The amount of Ac-DEVD-pNA cleaved in pmol/min is then calculated and plotted.

Analysis of Mitochondria Depolarization by Flow Cytometry: The depolarization of the mitochondrial membrane can be measured by the fluorescence emitted by the JC-9 dye (Molecular Probes, Eugene Oreg.). 100 μM of test compound or 10 μM etoposide in 1 μL of EtOH is added to cell culture flasks containing 50 mL of $10 \times 10^6$ U-937 cells/mL. After growth for 72 hours (37° C. in a 5% $CO_2$, 95% air atmosphere) the cells are harvested by centrifugation, counted, and diluted to $1 \times 10^6$ cells/mL in RPMI 1640 media. 10 microg of the JC-9 dye is added to $1 \times 10^6$ cells in 1 mL and incubated at room temperature for 10 min. Cells are washed twice with PBS and resuspended in a final volume of 500 μL PBS. The fluorescence intensity of each cell is determined by flow cytometry at 525 nm (channel 1 green) and 675 nm (channel 4 red). 50,000 cells are analyzed in each experiment. The data is then analyzed using Summit Software (Cytomation, Fort Collins Colo.) and the number of cells within the upper left region, viable cells, is determined.

Splenocyte Toxicity Assay: Splenocytes are isolated from the spleen of a 7-month old male C57Black/6 mouse and suspended in 1 mL RPMI 1640+10% FBS+2.5 microg/mL concanavalin A. These cells are counted and diluted so that $2.5 \times 10^5$ cells are seeded in to each well containing a total of 200 μL of media. Various concentrations of a test compound in 1 μL of EtOH are added and the plates are then incubated at 37° C. in a 5% $CO_2$, 95% air atmosphere for 72 hours. 1 μL of EtOH was added to separate control wells. After 72 hours of incubation, 20 μL of the MTS/PMS CellTiter 96 Cell Proliferation Assay reagent (Promega, Madison Wis.) is added to each well. The plates are incubated at 37° C. for approximately two hours until the colored product is formed and the absorbance is then measured at 490 nm in a Spectra Max Plus 384 plate reader (Molecular Devices, Sunnyvale Calif.).

T-cell Isolation and Toxicity Assay: Splenocytes are isolated from the spleen of a 3-month old male C57Black/6 mouse and suspended in 1 mL RPMI 1640+10% FBS. Erythrocytes are selectively lysed and the T cells highly enriched by using a mouse erythrocyte lysing kit and a mouse T cell enrichment column (R & D Systems, Minneapolis Minn.). FITC labeled anti-TCR antibodies are used to determine the purity of T cells in pre- and post-column samples. The T cells are enriched from approximately 35% to 90% of the total cell population. The purified T cells are then counted and diluted so that $2.5 \times 10^5$ cells are seeded in to each well of a 96-well plate containing 200 μL of media. These cells are either stimulated to grow (by addition of ConA to a concentration of 2.5 microg/mL) or left untreated. Various concentrations of test compound in 1 μL of EtOH or 1 μL of EtOH as a control are added and the plates incubated at 37° C. in a 5% $CO_2$, 95% air atmosphere for 72 hours. After the 72 hours of incubation, 200 μL of cells are diluted in 300 μL PBS. Propidium iodide is then added to a concentration of 1 microg/mL. Cells are then incubated at room temperature for 5 minutes and analyzed by flow cytometry. The fluorescence intensity of each cell is determined at 620 nm (channel 3) and at least 50,000 cells are analyzed for each experiment. The data is then analyzed using Summit Software (Cytomation, Fort Collins Colo.) and the number of viable cells determined. Non-concanavalin A stimulated T cells are also treated with test compound, and viable cells in these samples are determined by PI staining (as above). FITC labeled anti-TCR antibodies are used to determine the purity of T cells before and after purification.

Microscopy: U-937 cells from cell culture are harvested by centrifugation at 250×g for 5 minutes. Cells are resuspended in RPMI 1640+10% FBS, counted using a hemocyometer and diluted so that 20,000 cells were seeded in to each well of a 96-well plate. Media is then added to bring the total volume of each well to 100 μL. Test compound is added to make a final concentration of 100 μM. Pictures of the cells can be taken at various times using a Carl Zeiss confocal microscope (Carl Zeiss, Thornwood N.Y.).

Example 4

Identification of Small Molecules that Potently Induce Death in Melanoma Cells

A common trait of most cancers is the ability to evade the natural cell death process. Although healthy cells have tightly regulated mechanisms for apoptosis, or programmed cell death, cancerous cells often have multiple means by which they shut down this pathway and achieve immortality. Indeed, virtually every point on the apoptotic cascade has been exploited by cancer, from the p53 tumor suppressor that senses DNA damage and is inactivated in >50% of human cancers, to caspases that normally execute the apoptotic program and are mutated in certain circumstances. Thus a goal of many anti-cancer treatments is the restoration of proper apoptosis, and a significant number of anti-cancer drugs function by inducing apoptotic cell death.

The cell cycle is divided into four phases, G1, S (DNA synthesis), G2, and M (mitosis). Anti-cancer agents typically target the propensity of cancer cells to rapidly replicate their DNA and divide, and thus arrest cell growth in the synthesis (S) or mitosis (M) phase of the cell cycle. For instance, cisplatin, doxorubicin, and cyclophosphamide cause DNA damage and S phase arrest, while etoposide, taxol, and cholchicine all target operations that affect mitosis and ultimately result in G2/M arrest.

Currently, 75% of cancer deaths are due to epithelial cancers; some of these forms of cancer, such as advanced malignant melanoma, are largely incurable. The lethality of melanoma is due to the intrinsic resistance of malignant melanocytes to mechanisms of apoptotic death as induced by common anti-cancer drugs. The five-year survival rates for disseminated melanoma is <5% with an average survival time of 6 to 10 months. The lack of sensitivity of melanoma to chemotherapy has been well documented. Common anti-cancer drugs such as taxol, cisplatin, etoposide, doxorubicin and other several others showed no efficacy in large randomized trials, and even popular combination therapies have provided little benefits in melanoma patients. This lack of clinical efficacy is supported by in vitro studies testing drugs against melanoma cell lines. In fact, only one single-entity drug, dacarbazine (DTIC), has been approved by the FDA for treatment of melanoma, and this medicine provides complete remission in only 2% of patients. Thus, as common anti-cancer drugs are profoundly ineffective in the treatment of disseminated melanoma there is a clear need for compounds that are efficient killers of these cells and that act through non-standard anti-cancer mechanisms. Some urgency is needed in this regard as the lifetime risk for melanoma is increasing and now estimated at 1 in 75.

In their natural role as a protectant from the harmful effects of the sun, melanocytes are bombarded with UV light, a potent DNA damaging agent. Thus, it is not surprising that melanoma cells are exquisitely resistant to therapies targeting DNA synthesis and replication such as radiation and alkylating agents; indeed, some lines of evidence indicate that such treatments cause melanoma cells to proliferate instead of die. Examination of apoptotic and cell checkpoint proteins has explored how melanoma cells evade cell death and continue to proliferate. Certain melanomas have a methylation-inactivated Apaf-1 signaling complex, and/or up-regulation of the caspase-inhibiting surviving protein. In addition, a common chromosomal defect in melanoma cells is a deletion in the 9p21 region, resulting in the inactivation of the G1/S checkpoint through ablation of the p16INK4A protein.

Given the poor long-term survival prospects for late stage melanoma cancers and the lack of any effective treatments, the compounds we have discovered can provide important chemotherapeutic agents and further insights into combating melanoma and other cancers.

Several compounds described herein were synthesized and tested for activity in connection with the induction of cell death in cancer cells using the high-throughput cell death assay I described above. The cell line UACC-62 was used as an example of a melanoma cell line (source: National Cancer Institute; see, e.g., Plowman J., 1995, Cancer Res. 55(4):862-867. Compounds CX1-CX17 were tested and IC50 values measured upon exposure to UACC-62 cells; see Table 1. Several compounds having potencies in the submicromolar range were identified.

TABLE 1

Results of testing compounds in UACC-62 cells using High-throughput Cell Death Assay I

| Compound | IC50 (μM) at 72 hours |
|---|---|
| CX1 | 0.33 |
| CX2 | 0.29 |
| CX3 | 0.53 |
| CX4 | 0.64 |
| CX5 | 0.67 |
| CX6 | 0.72 |
| CX7 | 2.3 |
| CX8 | 2.5 |
| CX9 | 2.33 |
| CX10 | 4.21 |
| CX11 | 4.5 |
| CX12 | 4.6 |
| CX13 | 7.19, 13.8 |
| CX14 | 7.19 |
| CX15 | 16.5 |
| CX16 | 17.5 |
| CX17 | 51 |

Structures of compounds CX1-CX17 are given in Scheme 1.

Compound CX5 was further tested using the same high-throughput cell death assay I for activity in inducing death in multiple cell lines representing a variety of cancer types. This TPMP compound demonstrated considerable potency across a range of cancerous cells. See Table 2.

TABLE 2

Results of testing compound CX5 (diethyl derivative) in multiple cell lines representing a variety of cancer types.

| Cell line | Cancer type | diethyl TPMP IC$_{50}$ (μM) |
|---|---|---|
| B16-F10 | melanoma (mouse) | 0.81 |
| MDA-MB-231 | melanoma (human) | 1.09 |
| UACC-62 | melanoma (human) | 0.67 |
| SK-MEL-5 | melanoma (human) | 3.39 |
| CRL-1782 | melanoma (human) | 1.41 |
| U-937 | lymphoma (human) | 11.60 |
| HL-60 | leukemia (human) | 13.17 |
| K562 | leukemia (CML, human) | 3.27 |
| NCI-H226 | lung (human) | 6.56 |
| Hs578t | breast (human) | 13.17 |
| ACHN | renal (human) | 9.69 |
| SK-N-SH | neuroblastoma (human) | 1.80 |

Example 5

Additional Assays of the Efficacy of Induction of Cell Death

Scheme 6 reports IC50 values for induction of cell death in certain melanoma cell lines for exemplary compounds of this invention. Cell death was assessed after 72 hr by measurement of cell density using the sulphorhodamine B assay. (V. Vichai and K. Kirtikara (2006) Nature Protocols Vol. 1(3): 1112-1116. The values listed under the structures given in Scheme 6 are the ranges of values for the efficacy of the compounds against the UACC-62 and SK-MEL-5 melanoma cell lines.

SCHEME 6: Cell Death in Melanoma Cells

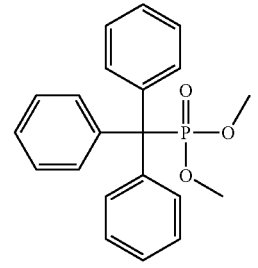

VN_X_12

11-28 uM

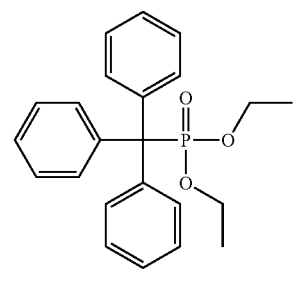

VN_X_4

10-14 uM

-continued
VN_X_23
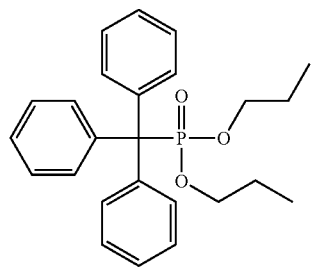
7-14 uM
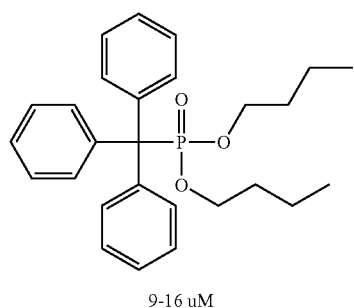
9-16 uM
VN_X_24
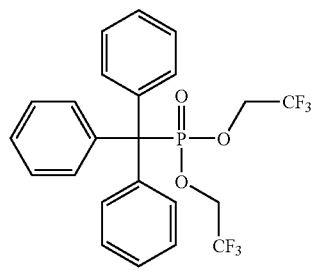
9-50 uM
VN_X_20
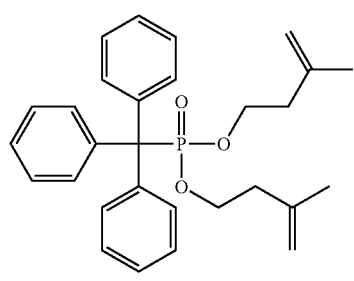
8-14 uM
VN_X_21
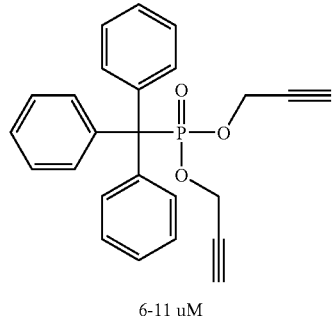
6-11 uM
VN_X_35
-continued
VN_X_22
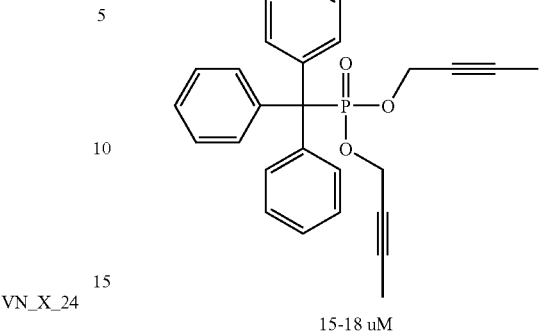
15-18 uM
VN_X_39
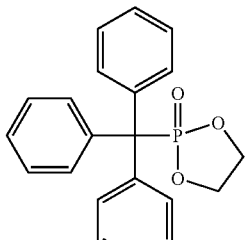
-100 uM
VN_X_37
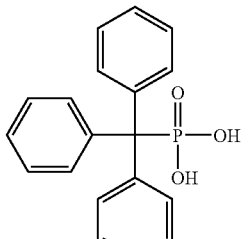
45-55 uM
VN_X_32
1-100 uM -continued
RPhos1
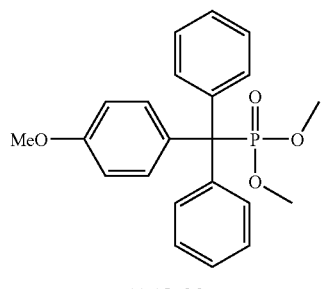
11-15 uM
RPhos2
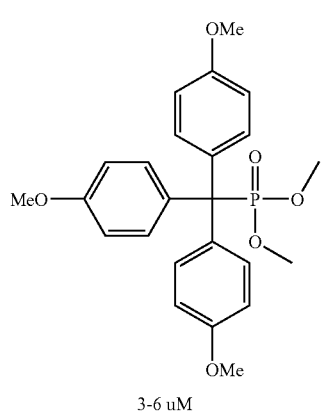
3-6 uM
RPhos4
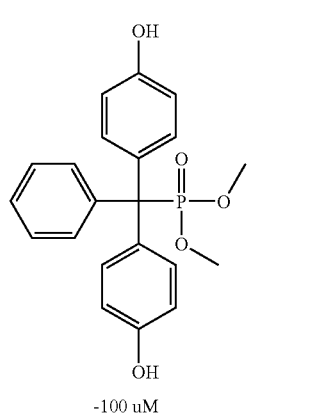
~100 uM
RPhos5
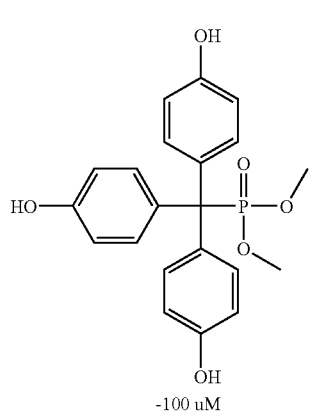
~100 uM
-continued
RPhos6
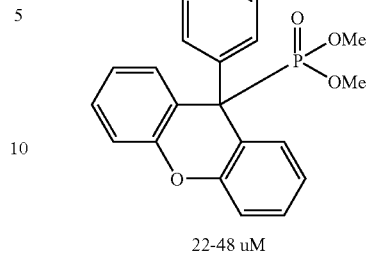
22-48 uM
RPhos7
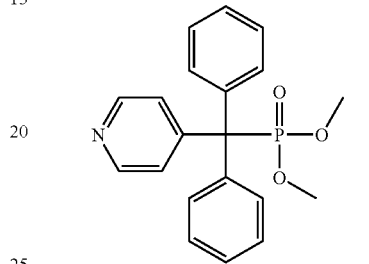
RPhos8
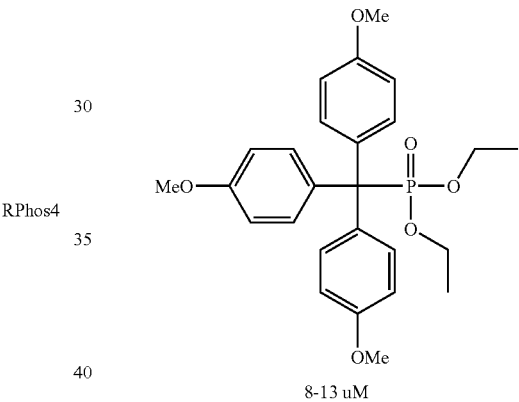
8-13 uM
VN_X_2
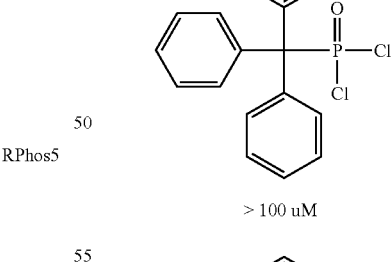
> 100 uM
VN_X_36
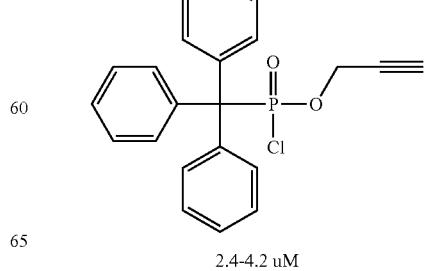
2.4-4.2 uM -continued

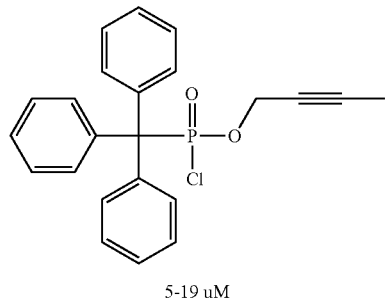

VN_X_25

5-19 uM

The sulphorhodamine B assay for assessing cell death is conducted as follows:

Cells (3000 in 198 uL of RPMI 1640 media) are pipetted into each well of a 96 well plate. 2 microliters of compound stock solutions (10 mM, 5 mM, 1 mM, 0.5 mM, 0.1 mM, 0.05 mM, 0.01 mM, 0.005 mM, 0.001 mM, 0.0005 mM, 0.0001 mM, 0.00005 mM) in 200 proof ethanol (obtained by serial dilution) are added to the plate in triplicate such that the following final concentrations are achieved: 100 microM, 50 microM, 10 microM, 5 microM, 1 microM, 0.5 microM, 0.1 microM, 0.05 microM, 0.01 microM, 0.005 microM, 0.001 microM, 0.0005 microM. The plates are incubated in a 37° C. 5% $CO_2$ incubator for 72 hours.

The medium is removed from the plate and each well is washed gently with 200 microL of PBS. Cold 10% trichloroacetic acid (200 microL) is added and the plates are placed in the 4° C. fridge for one hour. The trichloroacetic acid is removed and the plates are washed with 200 uL of deionized water (5 times). Sulphorhodamine B sodium salt (200 microL of 0.4%) in 1% acetic acid is added and the plates are allowed to sit at room temperature for 30 min. The plates are then washed with 1% acetic acid (5 times). Unbuffered Tris base (200 uL, 0 mM) is added and the plates are read on an absorbance plate reader at 510 nm after 30 minutes.

The invention has been described with reference to various specific and/or preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be employed in the practice of the invention as broadly disclosed herein without resort to undue experimentation; this can extend, for example, to starting materials, biological materials, reagents, synthetic methods, purification methods, analytical methods, assay methods, and biological methods other than those specifically exemplified. All art-known functional equivalents of the foregoing (e.g., compositions, methods, devices, device elements, materials, procedures and techniques, etc.) described herein are intended to be encompassed by this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, preferred embodiments, and optional features, modification and variation of the concepts herein disclosed may be resorted to by those skilled in the art, and that such modifications and variations are considered to be within the scope of this invention as defined by the appended claims.

REFERENCES

U.S. Provisional Application Ser. No. 60/516,566 by Hergenrother et al., filed Oct. 30, 2003; U.S. Provisional Patent Application Ser. No. 60/603,246 by Hergenrother et al., filed Aug. 20, 2004; U.S. Application Serial 10/976,186 filed Oct. 27, 2004 (US 20050197511, published Sep. 8, 2005); PCT Application PCT/US04/035746 filed Oct. 28, 2004 (WO2005/044191, published May 19, 2005).

U.S. Pat. Nos. 3,847,866; 3,702,879; 3,879,498; 4,463,159.

Nesterenko, V.; Byers, J. T.; Hergenrother, P. J. Org. Lett. 2003, 5, 281-284.

Monks A.; Scudiero D.; Johnson G.; Paull K.; Sausville E.; Mini-review. The NCI anti-cancer drug screen: a smart screen to identify effectors of novel targets; Anti-Cancer Drug Design October 1997, vol. 12, no. 7, pp. 533-541(9).

Alley, M. C., Scudiero, D. A., Monks, P. A., Hursey, M. L., Czerwinski, M. J., Fine, D. L., Abbott, B. J., Mayo, J. G., Shoemaker, R. H., and Boyd, M. R. Feasibility of Drug Screening with Panels of Human Tumor Cell Lines Using a Microculture Tetrazolium Assay. Cancer Research 48: 589-601, 1988.

Grever, M. R., Schepartz, S. A., and Chabner, B. A. The National Cancer Institute: Cancer Drug Discovery and Development Program. Seminars in Oncology, Vol. 19, No. 6, pp 622-638, 1992.

Boyd, M. R., and Paull, K. D. Some Practical Considerations and Applications of the National Cancer Institute In Vitro Anticancer Drug Discovery Screen. Drug Development Research 34: 91-109, 1995.

1) Hanahan, D.; Weinberg, R. A. "The hallmarks of cancer" *Cell* 2000, 100, 57-70.

2) Adjei, A. A.; Rowinsky, E. K. "Novel anticancer agents in clinical development" *Cancer Biol. Ther.* 2003, S1, S5-S15.

3) McGovern, V. J.; Balch, C. M.; Wilton, G. W. E.; Lippincott, J. B., Ed.; Cutaneous melanoma: clinical management and treatment results worldwide: Philadelphia, 1985, pp 2942.

4) Jemal, A.; Thomas, A.; Murray, T.; Thun, M. *CA Cancer J. Clin.* 2002, 52, 23-47.

5) Helmbach, H.; Rossmann, E.; Kern, M. A.; Schadendorf, D. "Drug-resistance in human melanoma" *Int. J. Cancer* 2001, 93, 617-622.

6) Serrone, L.; Zeuli, M.; Sega, F. M.; Cognetti, F. "Dacarbazine-based chemotherapy for metastatic melanoma: thirty-year experience overview." *J. Exp. Clin. Cancer Res.* 2000, 19, 21-34.

7) Soengas, M. S.; Lowe, S. W. "Apoptosis and melanoma chemoresistance" *Oncogene* 2003, 22, 3138-3151.

8) Middleton, M. R.; Lorigan, P.; Owen, J.; Ashcroft, L.; Lee, S. M.; Harper, P.; al, e. "A randomized phase III study comparing dacarbazine, BCNU, cisplatin and tamoxifen with dacarbazine and interferon in advanced melanoma" *Br. J. Cancer* 2000, 82, 1158-1162.

9) Schadendorf, D.; Worm, M.; Algermissen, B.; Kohlmus, C. M.; Czarnetzki, B. M. "Chemosensitivity testing of human malignant melanoma. A retrospective analysis of clinical response and in vitro drug sensitivity" *Cancer* 1994, 73, 103-108.

10) Anderson, C.; Buzaid, A.; Legha, S. "Systemic treatment for advanced cutaneous melanoma" *Oncology* 1995, 9, 1149-1154.

11) Lev, D. C.; Onn, A.; Melinkova, V. O.; Miller, C.; Stone, V.; Ruiz, M. "Exposure of melanoma cells to dacarbazine results in enhanced tumor growth and metastasis in vivo" *J. Clin. Oncol.* 2004, 22, 2092-2100.

12) Soengas, M. S.; Capodieci, P.; Polsky, D.; Mora, J.; Esteller, M.; Opitz-Araya, X.; McCombie, R.; Herman, J. G.; Gerald, W. L.; Lazebnik, Y. A.; Cordon-Cardo, C.; Lowe, S. W. "Inactivation of the apoptosis effector Apaf-1 in malignant melanoma" *Nature* 2001, 409, 207-211.

13) Grossman, D.; McNiff, J. M.; Li, F.; Altieri, D. C. "Expression and targeting of the apoptosis inhibitor, survivin, in human melanoma" *J. Invest. Dermatol.* 1999, 113, 1076-1081.

14) Cannon-Albright, L. A.; Goldgar, D. E.; Meyer, L. J.; Lewis, C. M.; Anderson, D. E.; Fountain, J. W.; Hegi, M. E.; Wiseman, R. W.; Petty, E. M.; Bale, A. E. "Assignment of a locus for familial melanoma, MLM, to chromosome 9p13-p22" *Science* 1992, 258, 1148-1152.

15) Fountain, J. W.; Karayiorgou, M.; Ernstoff, M. S.; Kirkwood, J. M.; Vlock, D. R.; Titus-Ernstoff, L.; Bouchard, B.; Vijayasaradhi, S.; Houghton, A. N.; Lahti, J. "Homozygous deletions within human chromosome band 9p21 in melanoma" *Proc. Natl. Acad. Sci.* 1992, 89, 10557-10561.

16) Nesterenko, V.; Putt, K. S.; Hergenrother, P. J. "Identification from a combinatorial library of a small molecule that selectively induces apoptosis in cancer cells" *J. Am. Chem. Soc.* 2003, 125(48): 14672-14673; December 3.

17) Konstantinov, S. M.; Topashka-Ancheva, M.; Benner, A.; Berger, M. R. "Alkylphosphocholines: Effects on human leukemic cell lines and normal bone marrow cells" *Int. J. Cancer* 1998, 77, 778-786.

18) de Graaff, M.; Maliepaard, M.; Pluim, D.; Floot, B. J.; Slaper-Cortenbach, I. C.; Schellens, J. H. "In vitro antagonistic cytotoxic interactions between platinum drugs and taxanes on bone marrow progenitor cell CFU-GM" *Anticancer Drugs* 1999, 10, 213-218.

19) LoRusso, P. M.; al., e. "Preclinical antitumor activity of XK469 (NSC 656889)" *Invest. New Drugs* 1999, 16, 287-296.

20) Qredipe, O. A.; Furbert-Harris, P. M.; Laniyan, I.; Griffin, W. M.; Sridhar, R. "Limits of stimulation of proliferation and differentiation of bone marrow cells of mice treated with swainsonine" *Internation. Immunopharm.* 2003, 3, 1537-1547.

21) Satyamoorthy, K.; Bogenrieder, T.; Herlyn, M. "No longer a molecular black box—new clues to apoptosis and drug resistance in melanoma" *Trends Mol. Med.* 2001, 7, 191-194.

22) Hergenrother P J. Obtaining and screening compound collections: a user's guide and a call to chemists. Curr Opin Chem Biol. 2006 May 2; PMID: 16677847

23) Silverman S K, Hergenrother P J. Combinatorial chemistry and molecular diversity Tools for molecular diversification and their applications in chemical biology. Curr Opin Chem Biol. 2006 May 3; PMID: 16675287

24) Goode D R, Sharma A K, Hergenrother P J. Using peptidic inhibitors to systematically probe the S1' site of caspase-3 and caspase-7. Org Lett. 2005 Aug. 4; 7(16): 3529-32. PMID: 16048334

25) Dothager R S, Putt K S, Allen B J, Leslie B J, Nesterenko V, Hergenrother P J. Synthesis and identification of small molecules that potently induce apoptosis in melanoma cells through G1 cell cycle arrest. J Am Chem Soc. 2005 Jun. 22; 127(24):8686-96. PMID: 15954774

26) Putt K S, Beilman G J, Hergenrother P J. Direct quantitation of poly(ADP-ribose) polymerase (PARP) activity as a means to distinguish necrotic and apoptotic death in cell and tissue samples. Chembiochem. 2005 January; 6(1):53-5. PMID: 15549722

27) Putt K S, Hergenrother P J. A nonradiometric, high-throughput assay for poly(ADP-ribose) glycohydrolase (PARG): application to inhibitor identification and evaluation. Anal Biochem. 2004 Oct. 15; 333(2):256-64. PMID: 15450800

28) Putt K S, Hergenrother P J. An enzymatic assay for poly(ADP-ribose) polymerase-1 (PARP-1) via the chemical quantitation of NAD(+): application to the high-throughput screening of small molecules as potential inhibitors. Anal Biochem. 2004 Mar. 1; 326(1):78-86. PMID: 14769338

The invention claimed is:

1. A compound having formula FX1:

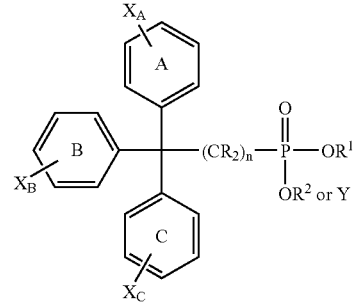

Formula FX1 wherein:

n is 0 or an integer from 1-6, inclusive;

Aryl rings A, B and C, independently of one another, are selected from the group consisting of or optionally substituted phenyl rings;

$X_A$, $X_B$, $X_C$ represent one or more hydrogens or non-hydrogen substituents independently selected from the group consisting of halogens, hydroxides, alkyl, alkenyl, alkynyl, alkoxide, thiol, thioalkoxide, ether, thioether, nitro, cyano, isocyano, cyanato, isocyanato, thiocyano, isothiocyano, amine (—N(R')$_2$), R'—CO—, R'O—CO—, (R')$_2$N—CO—, R'O—COO—, (R')$_2$N—COO—, (R')$_2$N—CONR', R'SO$_2$— and R'$_2$NSO$_2$— groups, wherein carbon atoms of these substituent groups are optionally substituted with one or more halogens, hydroxides, thiols, nitro groups, cyano groups, isocyano groups, cyanato groups, isocyanato groups, thiocyanato groups, or isothiocyano groups;

OR$^2$ is optionally replaced with Y which is a halogen; and

R$^1$ and R$^2$, independently of one another, are selected from the group consisting of alkenyl and alkynyl groups which are optionally substituted with one or more halogens, hydroxides, alkoxide, thiol, thioalkoxide, ether, thioether, amine (—N(R')$_2$), nitro, cyano, isocyano, cyanato, isocyanato, thiocyano, isothiocyano, R'—CO—, R'O—CO—, (R')$_2$N—CO—, R'O—COO—, (R')$_2$N—COO—, (R')$_2$N—CONR', R'SO$_2$—, or R'$_2$NSO$_2$— group;

where each R', independent of other R' in the molecule, are selected from the group consisting of hydrogen, alkyl, alkenyl, alkynyl, and aryl, optionally substituted with one or more halogen, hydroxide, alkyl, alkenyl, alkynyl, alkoxide, thiol, thioalkoxide, ether, thioether, nitro, cyano, isocyano, cyanato, isocyanato, thiocyano, isothiocyano, amine (—N(R')$_2$), R"CO—, (R")O—

CO—, (R")₂N—CO—, R")O—COO—, (R")₂N—COO—, (R")₂N—CONR", R"SO₂—, or R"₂NSO₂— groups; and where each R", independently of other R" in the molecule, are selected from the group consisting of hydrogen, alkyl, alkenyl, alkynyl, and aryl groups optionally substituted with one or more halogen, hydroxide, thiol, nitro, cyano, isocyano, cyanato, isocyanato, thiocyanato, or isothiocyano groups.

2. The compound of claim 1 wherein the A, B and C rings are phenyl rings or substituted phenyl rings carrying one or more hydroxyl groups, halogen atoms, alkyl groups having 1-6 carbon atoms alkoxide groups having 1-6 carbon atoms.

3. The compound of claim 1 where $X_A$, $X_B$ or $X_C$ represent one or more non-hydrogen substituents in the meta, para or both positions on the A, B or C rings.

4. The compound of claim 1 where each of $X_A$, $X_B$ and/or $X_C$ represent a single non-hydrogen substituent on a ring.

5. The compound of claim 1 where each of $X_A$, $X_B$ and/or $X_C$ represent a single halogen, hydroxide, alkyl having 1-6 carbon atoms or alkoxide having 1-6 carbon atoms on a ring.

6. The compound of claim 1 where each of $X_A$, $X_B$ and $X_C$ represents a single substituent in the para ring position wherein the substituent is a halogen, hydroxide, alkyl having 1-6 carbon atoms or alkoxide having 1-6 carbon atoms.

7. The compound of claim 1 where each of $X_A$, $X_B$ and/or $X_C$ represent a single substituent in the meta ring position wherein the substituent is a halogen, hydroxide, -alkyl having 1-6 carbon atoms or alkoxide having 1-6 carbon atoms.

8. The compound of claim 1 where n is 0.

9. The compound of claim 1 where $OR^2$ is not replaced with Y.

10. The compound of claim 1 where each of $X_A$, $X_B$ and $X_C$ are hydrogens.

11. Compound having formula FX3C:

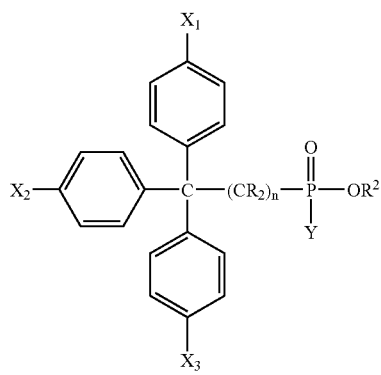

wherein:
Y is chlorine or $OR^1$;
n is 0 or 1;
$R^1$ and $R^2$, independently of one another, are selected from unsubstituted alkenyl groups having 2-6 carbon atoms or unsubstituted alkynyl groups having 2 to 6 carbon atoms; and
$X_1$, $X_2$ and $X_3$, independently of one another, are H, alkyl groups having 1-6 carbon atoms or alkoxide groups having 1-6 carbon atoms.

12. The compound of claim 11 wherein Y is chlorine.

13. The compound of claim 11 wherein n is 0.

14. The compound of claim 11 wherein $X_1$, $X_2$ and $X_3$ are hydrogens or alkoxide groups having 1-3 carbon atoms.

15. The compound of claim 11 wherein $X_1$, $X_2$ and $X_3$ are hydrogens or alkyl groups having 1-3 carbon atoms.

16. The compound of claim 1 having formula FX2:

Formula FX2

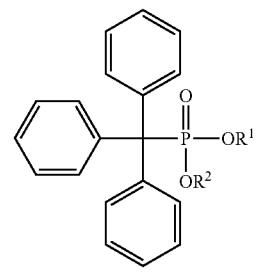

where $R^1$ and $R^2$ are alkenyl or alkynyl groups having 2-6 carbon atoms.

17. The compound of claim 1 having formula FX2B:

Formula FX2B

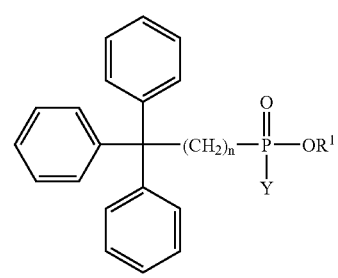

wherein Y is a halogen; and n is 0 or 1.

18. The compound of claim 1 having formula FX3A:

Formula FX3A

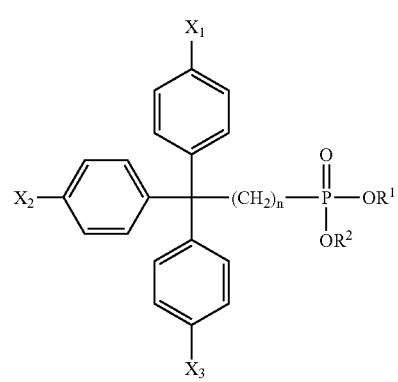

where
n is 0 or 1; and
$X_1$, $X_2$ and $X_3$, independently of one another, are hydrogens, halides, alkyl groups having 1-6 carbon atoms or alkoxide groups having 1-6 carbon atoms.

19. The compound of claim 1 having formula FX3B:

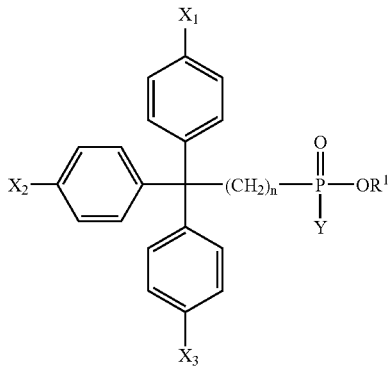
Formula FX3B where

Y is a halogen;

n is 0 or 1;

$X_1$, $X_2$ and $X_3$, independently of one another, are hydrogens, halides, alkyl groups having 1-6 carbon atoms or alkoxide groups having 1-6 carbon atoms.

20. The compound of claim 1 selected from the group consisting of compounds which have structures as follows:

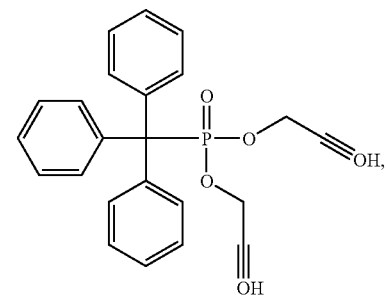
CX8

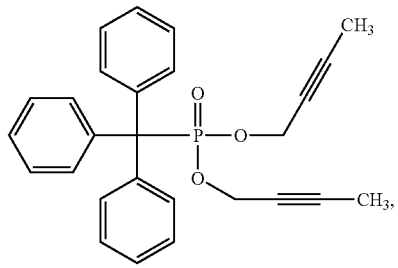
CX11

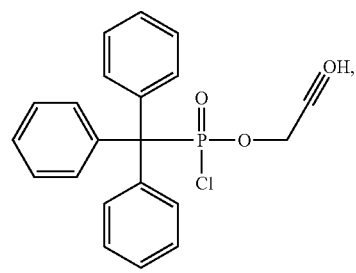
CX14

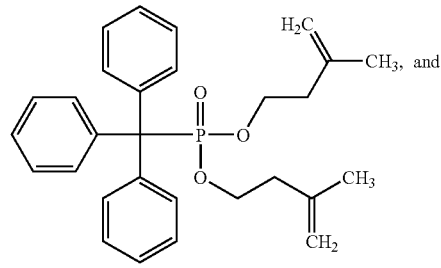
CX15

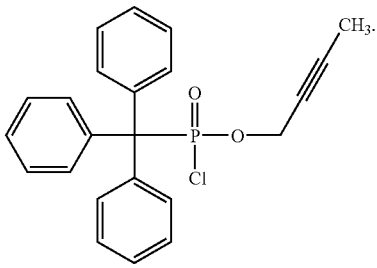
CX16

21. A pharmaceutical composition comprising a therapeutically effective amount of one or more compound of claim 1 and a pharmaceutically acceptable carrier or excipient.

22. The pharmaceutical composition of claim 21 further comprising a chemotherapeutic agent which damages DNA.

23. The pharmaceutical composition of claim 21 further comprising a chemotherapeutic agent which affects mitosis of a cell.

24. The compound of claim 1 where n is 0, $OR^2$ is replaced with Y and Y is a halogen.

25. The compound of claim 1 wherein n is 0 and $R^2$ is an alkynyl group having 2-6 carbon atoms.

26. The compound of claim 25 wherein $X_A$, $X_B$ and $X_C$ represent one or more hydrogens or non-hydrogen substituents independently selected from the group consisting of halogens, hydroxides, alkyl, alkenyl, alkynyl, and alkoxide groups.

27. The compound of claim 25 wherein $X_A$, $X_B$ and $X_C$ represent one or more hydrogens, halogens, or alkyl groups having 1-6 carbon atoms.

28. The compound of claim 25 wherein $X_A$, $X_B$ and $X_C$ represent one or more hydrogens, or alkyl groups having 1-6 carbon atoms.

29. The compound of claim 1 wherein n is 0, $OR^2$ is replaced by Y and Y is Cl, and $R^2$ is an alkynyl group having 2 or 3 carbon atoms.

30. The compound of claim 29 wherein $X_A$, $X_B$ and $X_C$ represent one or more hydrogens, halogens, or alkyl groups having 1-6 carbon atoms.

31. The compound of claim 29 wherein $X_A$, $X_B$ and $X_C$ all represent hydrogens or each represent a single non-hydrogen substituent in the para position on the A, B and C rings, wherein the substituent is selected from halogens, hydroxide and alkyl groups having 1-6 carbon atoms.

32. The compound of claim 31 wherein $X_A$, $X_B$ and $X_C$ each represent a single non-hydrogen substituent in the para position on the A, B and C rings, wherein the substituent is selected from alkyl groups having 1-6 carbon atoms.

33. The compound of claim 31 wherein $X_A$, $X_B$ and $X_C$ each represent a single non-hydrogen substituent in the para position on the A, B and C rings, wherein the substituent is selected from alkyl groups having 1-3 carbon atoms.

34. The compound of claim 33 wherein $X_A$, $X_B$ and $X_C$ each represent a single non-hydrogen substituent in the para position on the A, B and C rings, wherein the substituent is a methyl group.

35. A pharmaceutical composition comprising a therapeutically effective amount of one or more compound of claim 11 and a pharmaceutically acceptable carrier or excipient.

36. A pharmaceutical composition comprising a therapeutically effective amount of one or more compound of claim 24 and a pharmaceutically acceptable carrier or excipient.

37. A pharmaceutical composition comprising a therapeutically effective amount of one or more compound of claim 20 and a pharmaceutically acceptable carrier or excipient.

38. The compound of claim 1 wherein n is 0 or 1.

39. The compound of claim 38 wherein:

$R^1$ and $R^2$ are selected from the group consisting of alkenyl and alkynyl groups which are optionally substituted with one or more substituents selected from the group consisting of halogen, hydroxide, and alkoxide groups; and $X_A$, $X_B$ and $X_C$ represent one or more hydrogens or non-hydrogen substituents independently selected from the group consisting of halogens, hydroxides, alkyl, and alkoxide groups.

40. The compound of claim 1 wherein $R^1$ and $R^2$ are alkynes having 2-6 carbon atoms.

41. The compound of claim 1 wherein $OR^2$ is replaced with Y.

42. The compound of claim 1 wherein $OR^2$ is replaced with Y and Y is Cl.

43. The compound of claim 11 where Y is Cl and $X_1$, $X_2$ and $X_3$ are hydrogens or alkyl groups having 1-3 carbon atoms.

44. The compound of claim 43 where n is 0.

45. The compound of claim 11 wherein n is 0, Y is Cl, $X_1$, $X_2$ and $X_3$ are hydrogens or-alkyl groups having 1-3 carbon atoms and $R^2$ is an alkynyl group having 2-6 carbon atoms.

46. The compound of claim 11 where Y is $OR^1$.

47. The compound of claim 18 where $OR^2$ is not replaced with Y.

* * * * *